United States Patent
Cameron et al.

(10) Patent No.: US 10,039,320 B2
(45) Date of Patent: *Aug. 7, 2018

(54) MULTI-CHAMBERED VAPORIZER AND BLEND CONTROL

(71) Applicant: Lunatech, LLC, Encino, CA (US)

(72) Inventors: John Cameron, Encino, CA (US); Dean Becker, Fairhope, AL (US); Gene Fein, Oxnard, CA (US)

(73) Assignee: LunaTech, LLC, Encino, CA (US)

( * ) Notice: Subject to any disclaimer, the term of this patent is extended or adjusted under 35 U.S.C. 154(b) by 80 days.

This patent is subject to a terminal disclaimer.

(21) Appl. No.: 15/155,563

(22) Filed: May 16, 2016

(65) Prior Publication Data

US 2016/0331026 A1 Nov. 17, 2016

Related U.S. Application Data

(60) Provisional application No. 62/161,825, filed on May 14, 2015.

(51) Int. Cl.
| | |
|---|---|
| *A24F 11/00* | (2006.01) |
| *A24F 47/00* | (2006.01) |
| *A61M 15/06* | (2006.01) |
| *A61M 15/00* | (2006.01) |
| *A61M 11/04* | (2006.01) |
| A61M 16/00 | (2006.01) |

(52) U.S. Cl.
CPC .......... *A24F 47/002* (2013.01); *A24F 47/008* (2013.01); *A61M 11/042* (2014.02); *A61M 15/0085* (2013.01); *A61M 15/06* (2013.01); *A61M 2016/0039* (2013.01); *A61M 2205/332* (2013.01); *A61M 2205/3317* (2013.01); *A61M 2205/3368* (2013.01); *A61M 2205/3553* (2013.01); *A61M 2205/3592* (2013.01); *A61M 2205/3653* (2013.01); *A61M 2205/581* (2013.01); *A61M 2205/582* (2013.01); *A61M 2205/584* (2013.01); *A61M 2205/8206* (2013.01)

(58) Field of Classification Search
CPC ... A24F 47/002; A24F 47/008; A61M 11/042; A61M 15/0085; A61M 15/06; A61M 2016/0039; A61M 2205/3317
USPC ........................................................ 131/328
See application file for complete search history.

(56) References Cited

U.S. PATENT DOCUMENTS

| | | |
|---|---|---|
| 7,954,730 B2 | 6/2011 | Ng |
| 8,757,147 B2 | 6/2014 | Terry et al. |
| 8,820,330 B2 | 9/2014 | Bellinger |

(Continued)

*Primary Examiner* — Khiem Nguyen
(74) *Attorney, Agent, or Firm* — Susan L. McCain; Sergio Becerra; Hankin Patent Law, APC

(57) ABSTRACT

An electronic vapor device is disclosed comprising a vapor outlet, a first container for storing a first vaporizable material, wherein the first container is permanently integrated into the electronic vapor device, a second container for storing a second vaporizable material, wherein the second container is removable from the electronic vapor device, a docking bay configured to receive the second container, wherein the second container is removed from or inserted into the docking bay through a door, and a vaporizer component configured for vaporizing the first vaporizable material or the second vaporizable material to generate a vapor and for providing the vapor to the vapor outlet.

11 Claims, 22 Drawing Sheets

(56) References Cited

U.S. PATENT DOCUMENTS

| | | | |
|---|---|---|---|
| 8,851,083 B2 | 10/2014 | Oglesby et al. | |
| 8,955,522 B1 | 2/2015 | Bowen et al. | |
| 9,408,416 B2 | 8/2016 | Monsees et al. | |
| 9,498,002 B1 | 11/2016 | Soreide | |
| 9,585,981 B2 | 3/2017 | Wynalda, Jr. | |
| 9,763,478 B2 * | 9/2017 | Cameron | F01K 5/00 |
| 2007/0042792 A1 | 2/2007 | Perfetto et al. | |
| 2015/0161883 A1 | 6/2015 | Satgunam | |
| 2015/0181924 A1 | 7/2015 | Llamas | |
| 2015/0013695 A1 | 12/2015 | Righetti | |
| 2015/0351449 A1 | 12/2015 | Righetti | |
| 2016/0157524 A1 | 6/2016 | Bowen | |
| 2016/0198759 A1 | 7/2016 | Kuntawala | |
| 2016/0213866 A1 | 7/2016 | Tan | |
| 2016/0345621 A1 | 12/2016 | Li | |
| 2016/0366928 A1 | 12/2016 | Liu | |
| 2017/0079322 A1 | 3/2017 | Li et al. | |

\* cited by examiner

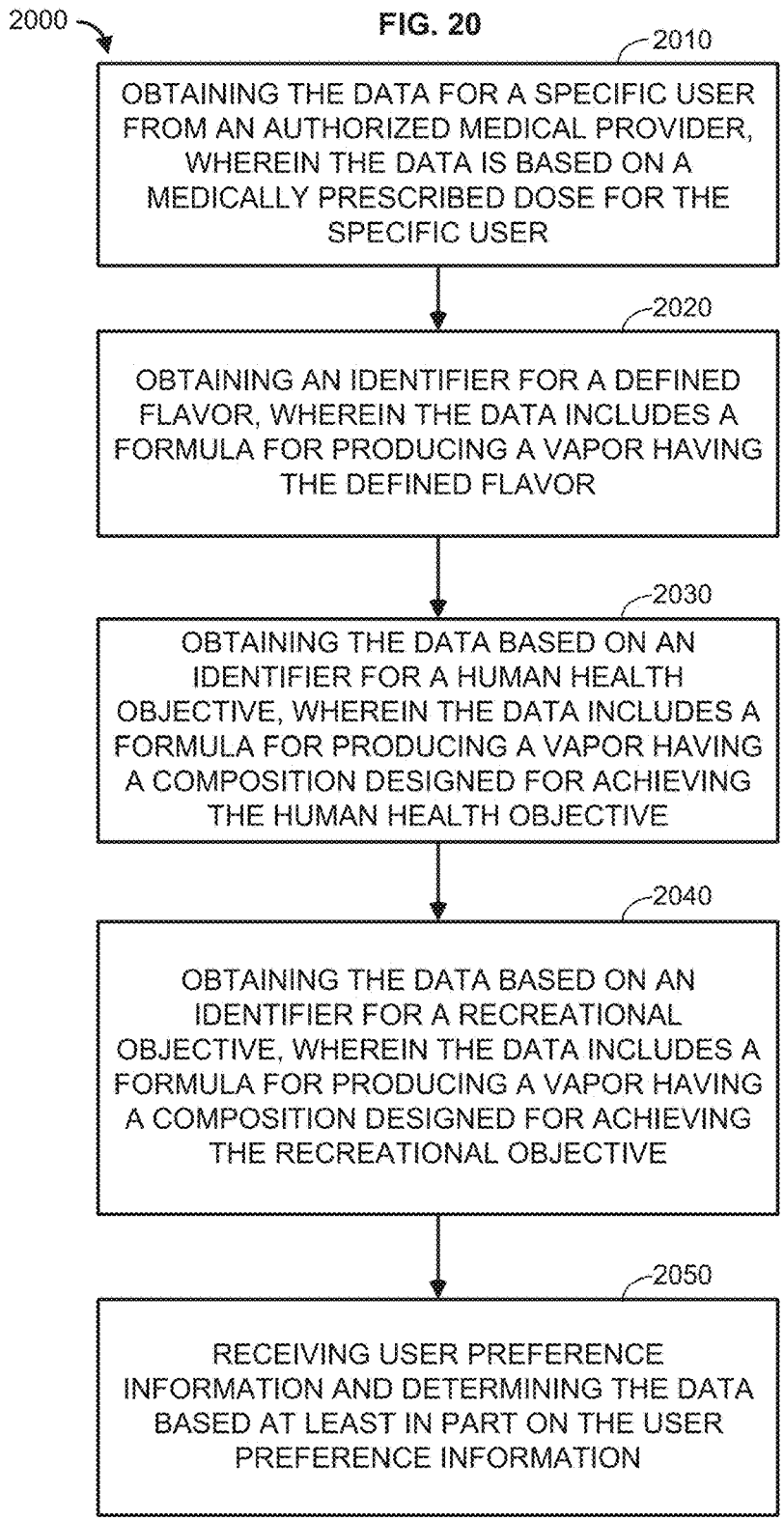

2010 — RECEIVING THE DATA FORMATTED ACCORDING TO A COMPUTER NETWORK PROTOCOL VIA A RECEIVER PORT COUPLED TO THE PROCESSOR

2020 — COMMUNICATING WITH AN EXTERNAL SERVER VIA A COMPUTER NETWORK TO OBTAIN THE DATA

2030 — CONFIRMING THAT THE DATA IS AUTHORIZED FOR CONTROLLING THE RELATIVE RATE, BASED ON AN ACCESS LICENSE GRANTED BY A USER OF THE APPARATUS TO AN IDENTIFIED PERSON

2040 — DETERMINING THE ACCESS LICENSE, BASED ON A RELATIONSHIP STATUS OF THE IDENTIFIED PERSON IN SOCIAL NETWORK DATA FOR THE USER OBTAINED FROM A SOCIAL NETWORKING SERVER

2210
DETERMINING A FIRST VAPORIZATION RATE AND A SECOND VAPORIZATION RATE

2220
VAPORIZING A FIRST VAPORIZABLE MATERIAL BASED ON THE FIRST VAPORIZATION RATE TO CREATE A FIRST VAPOR

2230
VAPORIZING A SECOND VAPORIZABLE MATERIAL BASED ON THE SECOND VAPORIZATION RATE TO CREATE A SECOND VAPOR

2240
EXPELLING THE FIRST VAPOR AND THE SECOND VAPOR THROUGH AN EXHAUST PORT FOR INHALATION BY A USER

MULTI-CHAMBERED VAPORIZER AND BLEND CONTROL

CROSS REFERENCE TO RELATED PATENT APPLICATION

This application claims priority to U.S. Provisional Application No. 62/161,825 filed May 14, 2015, incorporated herein by reference in its entirety.

BACKGROUND

Various types of personal vaporizers have been known in the art for many years. In general, such vaporizers are characterized by heating a solid to a smoldering point, vaporizing a liquid by heat, or nebulizing a liquid by heat and/or by expansion through a nozzle. Such devices are designed to release aromatic materials in the solid or liquid while avoiding high temperatures of combustion and associated formation of tars, carbon monoxide, or other harmful byproducts. Preferably, the device releases a vapor or very fine mist with a mouth feel similar to smoke, under suction. Thus, a vaporizing device can be made to mimic traditional smoking articles such as cigarettes, cigars, pipes and hookahs in certain aspects, while avoiding significant adverse health effects of traditional tobacco or other herbal consumption.

While various designs are long known, it is only relatively recently that technology has improved and markets have developed to the point to make mass-marketing of personal vaporizers practical. A large variety of rechargeable and disposal products have become popular. In both types of popular products on the market today, control of the vaporization products is generally limited to managing the supply of a vaporizing fluid at the point of production or recharging. In other words, once a vaporizing device is supplied with its vaporizing fluid, the composition of its output is predetermined. Accordingly, control of the output composition is not possible without replacing the vaporizing fluid or using a different device that has been supplied with a different fluid.

It would be desirable, therefore, to develop new technologies for controlling operation of a vaporizing or nebulizing device, that overcomes these and other limitations of the prior art, and enhances the utility of such devices.

SUMMARY

It is to be understood that both the following general description and the following detailed description are exemplary and explanatory only and are not restrictive. Disclosed is an electronic vapor device comprising a vapor outlet, a first container for storing a first vaporizable material, a second container for storing a second vaporizable material, a first vaporizer component coupled to the first container configured for vaporizing the first vaporizable material at a first vaporization rate to generate a first vapor and for providing the first vapor to the vapor outlet, and a second vaporizer component coupled to the processor the second container configured for vaporizing the second vaporizable material at a second vaporization rate to generate a second vapor and for providing the second vapor to the vapor outlet. The vaporizer component and the second vaporizer component can vaporize the first vaporizable material and the second vaporizable material, respectively, in serial or simultaneously.

In an aspect, a method is disclosed comprising determining a first vaporization rate and a second vaporization rate, vaporizing a first vaporizable material based on the first vaporization rate to create a first vapor, vaporizing a second vaporizable material based on the second vaporization rate to create a second vapor, and expelling the first vapor and the second vapor through an exhaust port for inhalation by a user.

Additional advantages will be set forth in part in the description which follows or can be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The features, nature, and advantages of the present disclosure will become more apparent from the detailed description set forth below when taken in conjunction with the drawings, in which like reference characters are used to identify like elements correspondingly throughout the specification and drawings.

FIG. 20 illustrates an exemplary method;

FIG. 21 illustrates an exemplary method; and

FIG. 22 illustrates an exemplary method.

DETAILED DESCRIPTION

Figure 1:
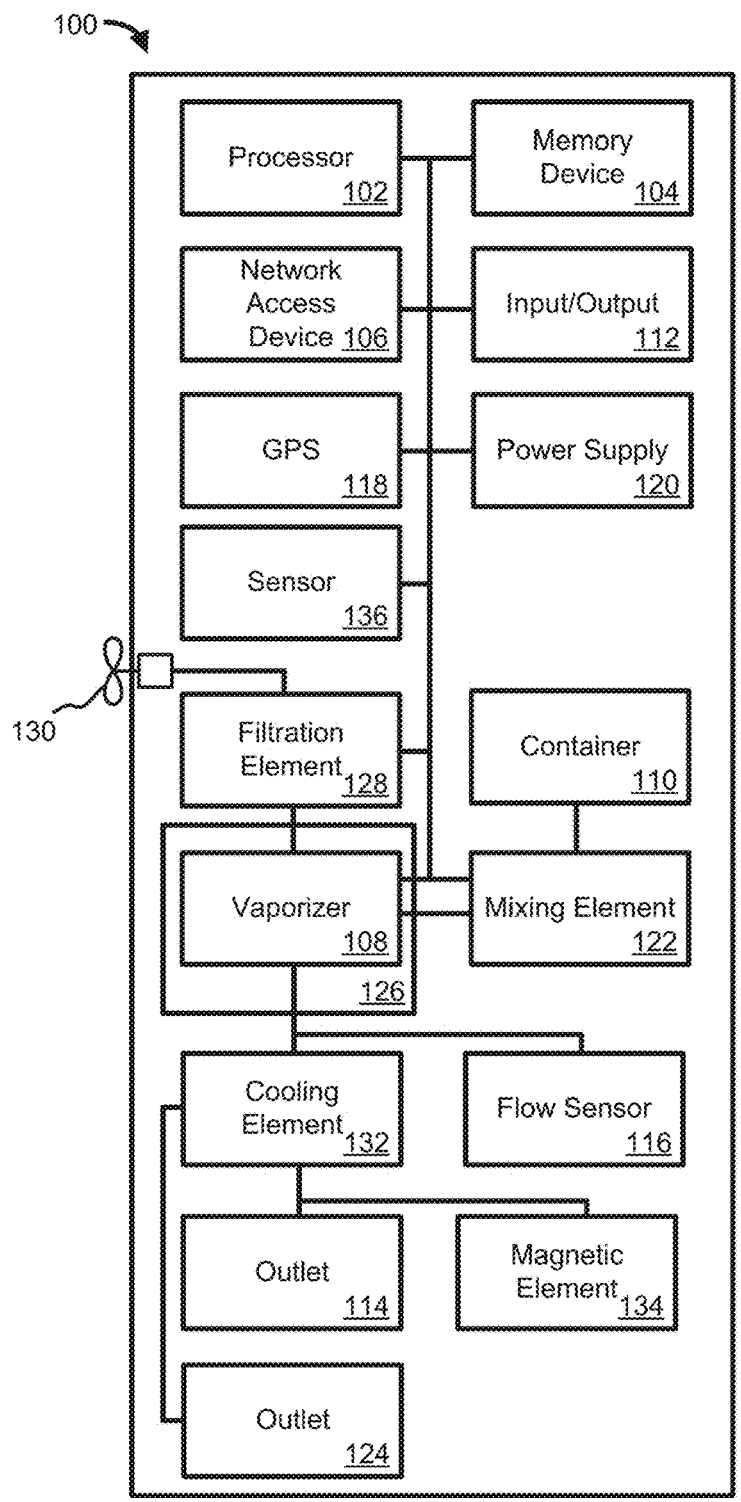
FIG. 1 illustrates a block diagram of an exemplary electronic vapor device.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems can be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium can be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions can be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Various aspects are now described with reference to the drawings. In the following description, for purposes of explanation, numerous specific details are set forth in order to provide a thorough understanding of one or more aspects. It can be evident, however, that the various aspects can be practiced without these specific details. In other instances, well-known structures and devices are shown in block diagram form in order to facilitate describing these aspects.

While embodiments of the disclosure are directed to vaporizing devices, it should be appreciated that aspects of the technology can be adapted by one of ordinary skill to nebulizing devices designed to produce an inhalable mist or aerosol.

The present disclosure relates to a multi-chambered vaporizing or nebulizing device, for example, an electronic device that uses a source of electrical power to vaporize or nebulize one or more contained fluids to produce an inhalable vapor or mist.

In an aspect of the disclosure, an assembly for vaporizing a fluid at a controlled rate is described. The assembly includes at least two containers of chambers each holding a different vaporizable material. A vaporizer is coupled to the at least two containers and configured to vaporize the different vaporizable materials. In operation, the vaporizer vaporizes or nebulizes the material, producing an inhalable mist. A processor or manual mechanism coupled to the vaporizer, configured to control a vaporization rate at which the vaporizer vaporizes the different vaporizable materials. In operation, the processor supplies a control signal to each vaporizer that controls the vaporization rate, for example by independently supplying power or otherwise independently controlling a rate of vaporization devices for each of the materials. In an alternative, or in addition, the mechanism for controlling vaporization rates may include one or more of a switch, dial, knob, slider, or push button, mechanically linked to a flow control element such as a valve or pump controlling supply of a fluid vaporizing material to the vaporizer. A receiver port may be coupled to the processor, and the processor may receive data determining each vaporization rate from the receiver port. Thus, the vaporization rate is controllable, by providing the data from a local or remote source, by manual input, or both. Any desired mix of materials in the multiple containers of the vaporizer may be supplied, and the mix may be changed dynamically during use to provide varied sensations or physiological effects. Data for changing the mix may be received during use.

Vaporizable fluids may be housed in multiple discrete chambers of the vaporizing device and mixed together in proscribed ratios in order to create a desired formula, which is then heated to be utilized as vapor by the end user(s). The mix of fluids may be stored in contiguous chambers with individual dispensers leading to an independent mixing point, so as to avoid unwanted residual mixing. The chambers may be made of metal, polycarbonate, polymer, natural material and may be refillable and cleanable.

The fluid combinations may be for health, recreational use, wellness or a combination thereof. The multi-chambered system may be vertically horizontally, or spherically configured, or may be a flexible bladder design.

The vaporization control system for the apparatus may be set to provide an initial fluid mix based upon default instructions via the system installation settings. These settings may then be changed, and/or the vaporizable fluids themselves may be changed or refilled. These changes may be initiated manually or via electronic configuring via local or remote electronic devices. These changes may also be pre-configured by the system. Such changes may be made via remote device of the user or any other user authorized by the user to whom the device is associated.

In related aspects, the assembly includes a memory device coupled to the processor, and the processor receives a user identifier or data for controlling the relative rates (e.g., each of the different vaporization rates, or a ratio of any two rates, or a rate factor for each vaporizer) and stores the user identifier or rate data in the memory device. The processor may generate data indicating a quantity of the different vaporizable materials consumed by the vaporizer in a defined period of time, and save the data in the memory device. The assembly may include a package substantially enclosing the at least two containers, the vaporizer, the processor, and other components. The package and assembly together may comprise one of: an electronic cigarette, an electronic cigar, an electronic hookah, or a hand-held personal vaporizer. The package and assembly may be designed to communicatively couple with a smart phone and/or notepad computer, which may provide user interface and control functions.

FIG. 1 is a block diagram of an exemplary electronic vapor device 100 as described herein. The electronic vapor device 100 can be, for example, an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like. The vapor device 100 can comprise any suitable housing for enclosing and protecting the various components disclosed herein. The vapor device 100 can comprise a processor 102. The processor 102 can be, or can comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™. The processor 102 can be coupled (e.g., communicatively, operatively, etc. . . . ) to auxiliary devices or modules of the vapor device 100 using a bus or other coupling. The vapor device 100 can comprise a power supply 110. The power supply 110 can comprise one or more batteries and/or other power storage device (e.g., capacitor) and/or a port for connecting to an external power supply. For example, an external power supply can supply power to the vapor device 100 and a battery can store at least a portion of the supplied power. The one or more batteries can be rechargeable. The one or more batteries can comprise a lithium-ion battery (including thin film lithium ion batteries), a lithium ion polymer battery, a nickel-cadmium battery, a nickel metal hydride battery, a lead-acid battery, combinations thereof, and the like. In an aspect, the power supply 110 can receive power via a power coupling to a case, wherein the vapor device 100 is stored in the case.

The vapor device 100 can comprise a memory device 104 coupled to the processor 102. The memory device 104 can comprise a random access memory (RAM) configured for storing program instructions and data for execution or processing by the processor 102 during control of the vapor device 100. When the vapor device 100 is powered off or in an inactive state, program instructions and data can be stored in a long-term memory, for example, a non-volatile magnetic optical, or electronic memory storage device (not shown). Either or both of the RAM or the long-term memory can comprise a non-transitory computer-readable medium storing program instructions that, when executed by the processor 102, cause the vapor device 100 to perform all or part of one or more methods and/or operations described herein. Program instructions can be written in any suitable high-level language, for example, C, C++, C# or the Java™, and compiled to produce machine-language code for execution by the processor 102.

In an aspect, the vapor device 100 can comprise a network access device 106 allowing the vapor device 100 to be coupled to one or more ancillary devices (not shown) such as via an access point (not shown) of a wireless telephone network, local area network, or other coupling to a wide area network, for example, the Internet. In that regard, the processor 102 can be configured to share data with the one or more ancillary devices via the network access device 106. The shared data can comprise, for example, usage data and/or operational data of the vapor device 100, a status of the vapor device 100, a status and/or operating condition of one or more the components of the vapor device 100, text to be used in a message, a product order, payment information, and/or any other data. Similarly, the processor 102 can be configured to receive control instructions from the one or more ancillary devices via the network access device 106. For example, a configuration of the vapor device 100, an operation of the vapor device 100, and/or other settings of the vapor device 100, can be controlled by the one or more ancillary devices via the network access device 106. For example, an ancillary device can comprise a server that can provide various services and another ancillary device can comprise a smartphone for controlling operation of the vapor device 100. In some aspects, the smartphone or another ancillary device can be used as a primary input/output of the vapor device 100 such that data is received by the vapor device 100 from the server, transmitted to the smartphone, and output on a display of the smartphone. In an aspect, data transmitted to the ancillary device can comprise a mixture of vaporizable material and/or instructions to release vapor. For example, the vapor device 100 can be configured to determine a need for the release of vapor into the atmosphere. The vapor device 100 can provide instructions via the network access device 106 to an ancillary device (e.g., another vapor device) to release vapor into the atmosphere.

In an aspect, data can be shared anonymously. The data can be shared over a transient data session with an ancillary device. The transient data session can comprise a session limit. The session limit can be based on one or more of a number of puffs, a time limit, and a total quantity of vaporizable material. The data can comprise usage data and/or a usage profile.

In an aspect, the vapor device 100 can also comprise an input/output device 112 coupled to one or more of the processor 102, a vaporizer 108, the network access device 106, and/or any other electronic component of the vapor device 100. Input can be received from a user or another device and/or output can be provided to a user or another device via the input/output device 112. The input/output device 112 can comprise any combinations of input and/or output devices such as buttons, knobs, keyboards, touchscreens, displays, light-emitting elements, a speaker, and/or the like. In an aspect, the input/output device 112 can comprise an interface port (not shown) such as a wired interface, for example a serial port, a Universal Serial Bus (USB) port, an Ethernet port, or other suitable wired connection. The input/output device 112 can comprise a wireless interface (not shown), for example a transceiver using any suitable wireless protocol, for example WiFi (IEEE 802.11), Bluetooth®, infrared, or other wireless standard. For example, the input/output device 112 can communicate with a smartphone via Bluetooth® such that the inputs and outputs of the smartphone can be used by the user to interface with the vapor device 100. In an aspect, the input/output device 112 can comprise a user interface. The user interface user interface can comprise at least one of lighted signal lights, gauges, boxes, forms, check marks, avatars, visual images, graphic designs, lists, active calibrations or calculations, 2D interactive fractal designs, 3D fractal designs, 2D and/or 3D representations of vapor devices and other interface system functions.

In an aspect, the input/output device 112 can be coupled to an adaptor device to receive power and/or send/receive data signals from an electronic device. For example, the input/output device 112 can be configured to receive power from the adaptor device and provide the power to the power supply 120 to recharge one or more batteries. The input/output device 112 can exchange data signals received from the adaptor device with the processor 102 to cause the processor to execute one or more functions.

In an aspect, the input/output device 112 can comprise a touchscreen interface and/or a biometric interface. For example, the input/output device 112 can include controls that allow the user to interact with and input information and commands to the vapor device 100. For example, with respect to the embodiments described herein, the input/output device 112 can comprise a touch screen display. The input/output device 112 can be configured to provide the content of the exemplary screen shots shown herein, which are presented to the user via the functionality of a display. User inputs to the touch screen display are processed by, for example, the input/output device 112 and/or the processor 102. The input/output device 112 can also be configured to process new content and communications to the system 100. The touch screen display can provide controls and menu selections, and process commands and requests. Application and content objects can be provided by the touch screen display. The input/output device 112 and/or the processor 102 can receive and interpret commands and other inputs, interface with the other components of the vapor device 100 as required. In an aspect, the touch screen display can enable a user to lock, unlock, or partially unlock or lock, the vapor device 100. The vapor device 100 can be transitioned from an idle and locked state into an open state by, for example, moving or dragging an icon on the screen of the vapor device 100, entering in a password/passcode, and the like. The input/output device 112 can thus display information to a user such as a puff count, an amount of vaporizable material remaining in the container 110, battery remaining, signal strength, combinations thereof, and the like.

In an aspect, the input/output device 112 can comprise an audio user interface. A microphone can be configured to receive audio signals and relay the audio signals to the input/output device 112. The audio user interface can be any interface that is responsive to voice or other audio commands. The audio user interface can be configured to cause an action, activate a function, etc, by the vapor device 100 (or another device) based on a received voice (or other audio) command. The audio user interface can be deployed directly on the vapor device 100 and/or via other electronic devices (e.g., electronic communication devices such as a smartphone, a smart watch, a tablet, a laptop, a dedicated audio user interface device, and the like). The audio user interface can be used to control the functionality of the vapor device 100. Such functionality can comprise, but is not limited to, custom mixing of vaporizable material (e.g., eLiquids) and/or ordering custom made eLiquid combinations via an eCommerce service (e.g., specifications of a user's custom flavor mix can be transmitted to an eCommerce service, so that an eLiquid provider can mix a custom eLiquid cartridge for the user). The user can then reorder the custom flavor mix anytime or even send it to friends as a present, all via the audio user interface. The user can also send via voice command a mixing recipe to other users. The other users can utilize the mixing recipe (e.g., via an electronic vapor device having multiple chambers for eLiquid) to sample the same mix via an auto-order to the other users' devices to create the received mixing recipe. A custom mix can be given a title by a user and/or can be defined by parts (e.g., one part liquid A and two parts liquid B). The audio user interface can also be utilized to create and send a custom message to other users, to join eVapor clubs, to receive eVapor chart information, and to conduct a wide range of social networking, location services and eCommerce activities. The audio user interface can be secured via a password (e.g., audio password) which features at least one of tone recognition, other voice quality recognition and, in one aspect, can utilize at least one special cadence as part of the audio password.

The input/output device 112 can be configured to interface with other devices, for example, exercise equipment, computing equipment, communications devices and/or other vapor devices, for example, via a physical or wireless connection. The input/output device 112 can thus exchange data with the other equipment. A user may sync their vapor device 100 to other devices, via programming attributes such as mutual dynamic link library (DLL) 'hooks'. This enables a smooth exchange of data between devices, as can a web interface between devices. The input/output device 112 can be used to upload one or more profiles to the other devices. Using exercise equipment as an example, the one or more profiles can comprise data such as workout routine data (e.g., timing, distance, settings, heart rate, etc. . . . ) and vaping data (e.g., eLiquid mixture recipes, supplements, vaping timing, etc. . . . ). Data from usage of previous exercise sessions can be archived and shared with new electronic vapor devices and/or new exercise equipment so that history and preferences may remain continuous and provide for simplified device settings, default settings, and recommended settings based upon the synthesis of current and archival data.

In an aspect, the vapor device 100 can comprise a vaporizer 108. In an aspect, the vapor device 100 can comprise a plurality of vaporizers 108. The vaporizer 108 can be coupled to one or more containers 110. In an aspect, the plurality of vaporizers 108 can each be coupled to a separate container. Each of the one or more containers 110 can be configured to hold one or more vaporizable or non-vaporizable materials. The vaporizer 108 can receive the one or more vaporizable or non-vaporizable materials from the one or more containers 110 and heat the one or more vaporizable or non-vaporizable materials until the one or more vaporizable or non-vaporizable materials achieve a vapor state. In various embodiments, instead of heating the one or more vaporizable or non-vaporizable materials, the vaporizer 108 can nebulize or otherwise cause the one or more vaporizable or non-vaporizable materials in the one or more containers 110 to reduce in size into particulates. In various embodiments, the one or more containers 110 can comprise a compressed liquid that can be released to the vaporizer 108 via a valve or another mechanism. In various embodiments, the one or more containers 110 can comprise a wick (not shown) through which the one or more vaporizable or non-vaporizable materials is drawn to the vaporizer 108. The one or more containers 110 can be made of any suitable structural material, such as, an organic polymer, metal, ceramic, composite, or glass material. In an aspect, the vaporizable material can comprise one or more of, a Propylene Glycol (PG) based liquid, a Vegetable Glycerin (VG) based liquid, a water based liquid, combinations thereof, and the like. In an aspect, the vaporizable material can comprise Tetrahydrocannabinol (THC), Cannabidiol (CBD), cannabinol (CBN), combinations thereof, and the like. In a further aspect, the vaporizable material can comprise an extract from *duboisia hopwoodii*.

In an aspect, the vapor device 100 can comprise a mixing element 122. The mixing element 122 can be coupled to the processor 102 to receive one or more control signals. The one or more control signals can instruct the mixing element 122 to withdraw specific amounts of fluid from the one or more containers 110. The mixing element can, in response to a control signal from the processor 102, withdraw select quantities of vaporizable material in order to create a customized mixture of different types of vaporizable material. The liquid withdrawn by the mixing element 122 can be provided to the vaporizer 108.

The vapor device 100 may include a plurality of valves, wherein a respective one of the valves is interposed between the vaporizer 108 and a corresponding one of outlet 114 and/or outlet 124 (e.g., one or more inlets of flexible tubes). Each of the valves may control a flow rate through a respective one of the flexible tubes. For example, each of the plurality of valves may include a lumen of adjustable effective diameter for controlling a rate of vapor flow there through. The assembly may include an actuator, for example a motor, configured to independently adjust respective ones of the valves under control of the processor. The actuator may include a handle or the like to permit manual valve adjustment by the user. The motor or actuator can be coupled to a uniform flange or rotating spindle coupled to the valves and configured for controlling the flow of vapor through each of the valves. Each of the valves can be adjusted so that each of the flexible tubes accommodate the same (equal) rate of vapor flow, or different rates of flow. The processor 102 can be configured to determine settings for the respective ones of the valves each based on at least one of: a selected user preference or an amount of suction applied to a corresponding one of the flexible tubes. A user preference can be determined by the processor 102 based on a user input, which can be electrical or mechanical. An electrical input can be provided, for example, by a touchscreen, keypad, switch, or potentiometer (e.g., the input/output 112). A mechanical input can be provided, for example, by applying suction to a mouthpiece of a tube, turning a valve handle, or moving a gate piece.

The vapor device 100 may further include at least one light-emitting element positioned on or near each of the outlet 114 and/or the outlet 124 (e.g., flexible tubes) and configured to illuminate in response to suction applied to the outlet 114 and/or the outlet 124. At least one of an intensity of illumination or a pattern of alternating between an illuminated state and a non-illuminated state can be adjusted based on an amount of suction. One or more of the at least one light-emitting element, or another light-emitting element, may illuminate based on an amount of vaporizable material available. For example, at least one of an intensity of illumination or a pattern of alternating between an illuminated state and a non-illuminated state can be adjusted based on an amount of the vaporizable material within the vapor device 100. In some aspects, the vapor device 100 may include at least two light-emitting elements positioned on each of the outlet 114 and/or the outlet 124. Each of the at least two light-emitting elements may include a first light-emitting element and an outer light-emitting element positioned nearer the end of the outlet 114 and/or the outlet 124 than the first light-emitting element. Illumination of the at least two light-emitting elements may indicate a direction of a flow of vapor.

In an aspect, input from the input/output device 112 can be used by the processor 102 to cause the vaporizer 108 to vaporize the one or more vaporizable or non-vaporizable materials. For example, a user can depress a button, causing the vaporizer 108 to start vaporizing the one or more vaporizable or non-vaporizable materials. A user can then draw on an outlet 114 to inhale the vapor. In various aspects, the processor 102 can control vapor production and flow to the outlet 114 based on data detected by a flow sensor 116. For example, as a user draws on the outlet 114, the flow sensor 116 can detect the resultant pressure and provide a signal to the processor 102. In response, the processor 102 can cause the vaporizer 108 to begin vaporizing the one or more vaporizable or non-vaporizable materials, terminate vaporizing the one or more vaporizable or non-vaporizable materials, and/or otherwise adjust a rate of vaporization of the one or more vaporizable or non-vaporizable materials. The processor 102 can also determine a vaporization rate. The vaporization rate can be an amount of vaporizable material vaporized over time. In an aspect, a vaporization rate can be determined based on a vaporizable material. In another aspect, a vaporization rate can be determined for each of a plurality of vaporizable materials. For example, in an embodiment of the vapor device 100 comprising two different vaporizable materials, each vaporizable material can have a vaporization rate. As a result, both vaporizable materials can be vaporized at the respective vaporization rate and the resulting vapors can be combined. In another aspect, the vaporization rates can be used to determine an amount of each vaporizable material to withdraw into the mixing element 122. The resulting mixture of vaporizable material can then be vaporized. In a further aspect, each container 110 can comprise an independent vaporizer 108 configured to vaporize vaporizable material contained in a corresponding container 110 at a vaporization rate. As a result, the different vaporizable materials can be vaporized independently, yet simultaneously or serially. Vaporization can be performed according to a vaporization rate determined for each vaporizable material.

In another aspect, the vapor can exit the vapor device 100 through an outlet 124. The outlet 124 differs from the outlet 114 in that the outlet 124 can be configured to distribute the vapor into the local atmosphere, rather than being inhaled by a user. In an aspect, vapor exiting the outlet 124 can be at least one of aromatic, medicinal, recreational, and/or wellness related. In an aspect, the vapor device 100 can comprise any number of outlets. In an aspect, the outlet 114 and/or the outlet 124 can comprise at least one flexible tube. For example, a lumen of the at least one flexible tube can be in fluid communication with one or more components (e.g., a first container) of the vapor device 100 to provide vapor to a user. In more detailed aspects, the at least one flexible tube may include at least two flexible tubes. Accordingly, the vapor device 100 may further include a second container configured to receive a second vaporizable material such that a first flexible tube can receive vapor from the first vaporizable material and a second flexible tube receive vapor from the second vaporizable material. For example, the at least two flexible tubes can be in fluid communication with the first container and with second container. The vapor device 100 may include an electrical or mechanical sensor configured to sense a pressure level, and therefore suction, in an interior of the flexible tube. Application of suction may activate the vapor device 100 and cause vapor to flow.

In another aspect, the vapor device 100 can comprise a piezoelectric dispersing element. In some aspects, the piezoelectric dispersing element can be charged by a battery, and can be driven by a processor on a circuit board. The circuit board can be produced using a polyimide such as Kapton, or other suitable material. The piezoelectric dispersing element can comprise a thin metal disc which causes dispersion of the fluid fed into the dispersing element via the wick or other soaked piece of organic material through vibration. Once in contact with the piezoelectric dispersing element, the vaporizable material (e.g., fluid) can be vaporized (e.g., turned into vapor or mist) and the vapor can be dispersed via a system pump and/or a sucking action of the user. In some aspects, the piezoelectric dispersing element can cause dispersion of the vaporizable material by producing ultrasonic vibrations. An electric field applied to a piezoelectric material within the piezoelectric element can cause ultrasonic expansion and contraction of the piezoelectric material, resulting in ultrasonic vibrations to the disc. The ultrasonic vibrations can cause the vaporizable material to disperse, thus forming a vapor or mist from the vaporizable material.

In some aspects, the connection between a power supply and the piezoelectric dispersing element can be facilitated using one or more conductive coils. The conductive coils can provide an ultrasonic power input to the piezoelectric dispersing element. For example, the signal carried by the coil can have a frequency of approximately 107.8 kHz. In some aspects, the piezoelectric dispersing element can comprise a piezoelectric dispersing element that can receive the ultrasonic signal transmitted from the power supply through the coils, and can cause vaporization of the vaporizable liquid by producing ultrasonic vibrations. An ultrasonic electric field applied to a piezoelectric material within the piezoelectric element causes ultrasonic expansion and contraction of the piezoelectric material, resulting in ultrasonic vibrations according to the frequency of the signal. The vaporizable liquid can be vibrated by the ultrasonic energy produced by the piezoelectric dispersing element, thus causing dispersal and/or atomization of the liquid. In an aspect, the vapor device 100 can be configured to permit a user to select between using a heating element of the vaporizer 108 or the piezoelectric dispersing element. In another aspect, the vapor device 100 can be configured to permit a user to utilize both a heating element of the vaporizer 108 and the piezoelectric dispersing element.

In an aspect, the vapor device 100 can comprise a heating casing 126. The heating casing 126 can enclose one or more of the container 110, the vaporizer 108, and/or the outlet 114. In a further aspect, the heating casing 126 can enclose one or more components that make up the container 110, the vaporizer 108, and/or the outlet 114. The heating casing 126 can be made of ceramic, metal, and/or porcelain. The heating casing 126 can have varying thickness. In an aspect, the heating casing 126 can be coupled to the power supply 120 to receive power to heat the heating casing 126. In another aspect, the heating casing 126 can be coupled to the vaporizer 108 to heat the heating casing 126. In another aspect, the heating casing 126 can serve an insulation role.

In an aspect, the vapor device 100 can comprise a filtration element 128. The filtration element 128 can be configured to remove (e.g., filter, purify, etc) contaminants from air entering the vapor device 100. The filtration element 128 can optionally comprise a fan 130 to assist in delivering air to the filtration element 128. The vapor device 100 can be configured to intake air into the filtration element 128, filter the air, and pass the filtered air to the vaporizer 108 for use in vaporizing the one or more vaporizable or non-vaporizable materials. In another aspect, the vapor device 100 can be configured to intake air into the filtration element 128, filter the air, and bypass the vaporizer 108 by passing the filtered air directly to the outlet 114 for inhalation by a user.

In an aspect, the filtration element 128 can comprise cotton, polymer, wool, satin, meta materials and the like. The filtration element 128 can comprise a filter material that at least one airborne particle and/or undesired gas by a mechanical mechanism, an electrical mechanism, and/or a chemical mechanism. The filter material can comprise one or more pieces of a filter fabric that can filter out one or more airborne particles and/or gasses. The filter fabric can be a woven and/or non-woven material. The filter fabric can be made from natural fibers (e.g., cotton, wool, etc.) and/or from synthetic fibers (e.g., polyester, nylon, polypropylene, etc.). The thickness of the filter fabric can be varied depending on the desired filter efficiencies and/or the region of the apparel where the filter fabric is to be used. The filter fabric can be designed to filter airborne particles and/or gasses by mechanical mechanisms (e.g., weave density), by electrical mechanisms (e.g., charged fibers, charged metals, etc.), and/or by chemical mechanisms (e.g., absorptive charcoal particles, adsorptive materials, etc.). In as aspect, the filter material can comprise electrically charged fibers such as, but not limited to, FILTRETE by 3M. In another aspect, the filter material can comprise a high density material similar to material used for medical masks which are used by medical personnel in doctors' offices, hospitals, and the like. In an aspect, the filter material can be treated with an anti-bacterial solution and/or otherwise made from anti-bacterial materials. In another aspect, the filtration element 128 can comprise electrostatic plates, ultraviolet light, a HEPA filter, combinations thereof, and the like.

In an aspect, the vapor device 100 can comprise a cooling element 132. The cooling element 132 can be configured to cool vapor exiting the vaporizer 108 prior to passing through the outlet 114. The cooling element 132 can cool vapor by utilizing air or space within the vapor device 100. The air used by the cooling element 132 can be either static (existing in the vapor device 100) or drawn into an intake and through the cooling element 132 and the vapor device 100. The intake can comprise various pumping, pressure, fan, or other intake systems for drawing air into the cooling element 132. In an aspect, the cooling element 132 can reside separately or can be integrated the vaporizer 108. The cooling element 132 can be a single cooled electronic element within a tube or space and/or the cooling element 132 can be configured as a series of coils or as a grid like structure. The materials for the cooling element 132 can be metal, liquid, polymer, natural substance, synthetic substance, air, or any combination thereof. The cooling element 132 can be powered by the power supply 120, by a separate battery (not shown), or other power source (not shown) including the use of excess heat energy created by the vaporizer 108 being converted to energy used for cooling by virtue of a small turbine or pressure system to convert the energy. Heat differentials between the vaporizer 108 and the cooling element 132 can also be converted to energy utilizing commonly known geothermal energy principles.

In an aspect, the vapor device 100 can comprise a magnetic element 134. For example, the magnetic element 134 can comprise an electromagnet, a ceramic magnet, a ferrite magnet, and/or the like. The magnetic element 134 can be configured to apply a magnetic field to air as it is brought into the vapor device 100, in the vaporizer 108, and/or as vapor exits the outlet 114.

The input/output device 112 can be used to select whether vapor exiting the outlet 114 should be cooled or not cooled and/or heated or not heated and/or magnetized or not magnetized. For example, a user can use the input/output device 112 to selectively cool vapor at times and not cool vapor at other times. The user can use the input/output device 112 to selectively heat vapor at times and not heat vapor at other times. The user can use the input/output device 112 to selectively magnetize vapor at times and not magnetize vapor at other times. The user can further use the input/output device 112 to select a desired smoothness, temperature, and/or range of temperatures. The user can adjust the temperature of the vapor by selecting or clicking on a clickable setting on a part of the vapor device 100. The user can use, for example, a graphical user interface (GUI) or a mechanical input enabled by virtue of clicking a rotational mechanism at either end of the vapor device 100.

In an aspect, cooling control can be set within the vapor device 100 settings via the processor 102 and system software (e.g., dynamic linked libraries). The memory 104 can store settings. Suggestions and remote settings can be communicated to and/or from the vapor device 100 via the input/output device 112 and/or the network access device 106. Cooling of the vapor can be set and calibrated between heating and cooling mechanisms to what is deemed an ideal temperature by the manufacturer of the vapor device 100 for the vaporizable material. For example, a temperature can be set such that resultant vapor delivers the coolest feeling to the average user but does not present any health risk to the user by virtue of the vapor being too cold, including the potential for rapid expansion of cooled vapor within the lungs and the damaging of tissue by vapor which has been cooled to a temperature which may cause frostbite like symptoms.

In an aspect, the vapor device 100 can be configured to receive air, smoke, vapor or other material and analyze the contents of the air, smoke, vapor or other material using one or more sensors 136 in order to at least one of analyze, classify, compare, validate, refute, and/or catalogue the same. A result of the analysis can be, for example, an identification of at least one of medical, recreational, homeopathic, olfactory elements, spices, other cooking ingredients, ingredients analysis from food products, fuel analysis, pharmaceutical analysis, genetic modification testing analysis, dating, fossil and/or relic analysis and the like. The vapor device 100 can pass utilize, for example, mass spectrometry, PH testing, genetic testing, particle and/or cellular testing, sensor based testing and other diagnostic and wellness testing either via locally available components or by transmitting data to a remote system for analysis.

In an aspect, a user can create a custom scent by using the vapor device 100 to intake air elements, where the vapor device 100 (or third-party networked device) analyzes the olfactory elements and/or biological elements within the sample and then formulates a replica scent within the vapor device 100 (or third-party networked device) that can be accessed by the user instantly, at a later date, with the ability to purchase this custom scent from a networked ecommerce portal.

In another aspect, the one or more sensors 136 can be configured to sense negative environmental conditions (e.g., adverse weather, smoke, fire, chemicals (e.g., such as CO2 or formaldehyde), adverse pollution, and/or disease outbreaks, and the like). The one or more sensors 136 can comprise one or more of, a biochemical/chemical sensor, a thermal sensor, a radiation sensor, a mechanical sensor, an optical sensor, a mechanical sensor, a magnetic sensor, an electrical sensor, combinations thereof and the like. The biochemical/chemical sensor can be configured to detect one or more biochemical/chemicals causing a negative environmental condition such as, but not limited to, smoke, a vapor, a gas, a liquid, a solid, an odor, combinations thereof, and/or the like. The biochemical/chemical sensor can comprise one or more of a mass spectrometer, a conducting/nonconducting regions sensor, a SAW sensor, a quartz microbalance sensor, a conductive composite sensor, a chemiresitor, a metal oxide gas sensor, an organic gas sensor, a MOSFET, a piezoelectric device, an infrared sensor, a sintered metal oxide sensor, a Pd-gate MOSFET, a metal FET structure, a electrochemical cell, a conducting polymer sensor, a catalytic gas sensor, an organic semiconducting gas sensor, a solid electrolyte gas sensors, a piezoelectric quartz crystal sensor, and/or combinations thereof.

The thermal sensor can be configured to detect temperature, heat, heat flow, entropy, heat capacity, combinations thereof, and the like. Exemplary thermal sensors include, but are not limited to, thermocouples, such as a semiconducting thermocouples, noise thermometry, thermoswitches, thermistors, metal thermoresistors, semiconducting thermoresistors, thermodiodes, thermotransistors, calorimeters, thermometers, indicators, and fiber optics.

The radiation sensor can be configured to detect gamma rays, X-rays, ultra-violet rays, visible, infrared, microwaves and radio waves. Exemplary radiation sensors include, but are not limited to, nuclear radiation microsensors, such as scintillation counters and solid state detectors, ultra-violet, visible and near infrared radiation microsensors, such as photoconductive cells, photodiodes, phototransistors, infrared radiation microsensors, such as photoconductive IR sensors and pyroelectric sensors.

The optical sensor can be configured to detect visible, near infrared, and infrared waves. The mechanical sensor can be configured to detect displacement, velocity, acceleration, force, torque, pressure, mass, flow, acoustic wavelength, and amplitude. Exemplary mechanical sensors include, but are not limited to, displacement microsensors, capacitive and inductive displacement sensors, optical displacement sensors, ultrasonic displacement sensors, pyroelectric, velocity and flow microsensors, transistor flow microsensors, acceleration microsensors, piezoresistive microaccelerometers, force, pressure and strain microsensors, and piezoelectric crystal sensors. The magnetic sensor can be configured to detect magnetic field, flux, magnetic moment, magnetization, and magnetic permeability. The electrical sensor can be configured to detect charge, current, voltage, resistance, conductance, capacitance, inductance, dielectric permittivity, polarization and frequency.

Upon sensing a negative environmental condition, the one or more sensors 122 can provide data to the processor 102 to determine the nature of the negative environmental condition and to generate/transmit one or more alerts based on the negative environmental condition. The one or more alerts can be deployed to the vapor device 100 user's wireless device and/or synced accounts. For example, the network device access device 106 can be used to transmit the one or more alerts directly (e.g., via Bluetooth®) to a user's smartphone to provide information to the user. In another aspect, the network access device 106 can be used to transmit sensed information and/or the one or more alerts to a remote server for use in syncing one or more other devices used by the user (e.g., other vapor devices, other electronic devices (smartphones, tablets, laptops, etc. . . . ). In another aspect, the one or more alerts can be provided to the user of the vapor device 100 via vibrations, audio, colors, and the like deployed from the mask, for example through the input/output device 112. For example, the input/output device 112 can comprise a small vibrating motor to alert the user to one or more sensed conditions via tactile sensation. In another example, the input/output device 112 can comprise one or more LED's of various colors to provide visual information to the user. In another example, the input/output device 112 can comprise one or more speakers that can provide audio information to the user. For example, various patterns of beeps, sounds, and/or voice recordings can be utilized to provide the audio information to the user. In another example, the input/output device 112 can comprise an LCD screen/touchscreen that provides a summary and/or detailed information regarding the negative environmental condition and/or the one or more alerts.

In another aspect, upon sensing a negative environmental condition, the one or more sensors 136 can provide data to the processor 102 to determine the nature of the negative environmental condition and to provide a recommendation for mitigating and/or to actively mitigate the negative environmental condition. Mitigating the negative environmental conditions can comprise, for example, applying a filtration system, a fan, a fire suppression system, engaging a HVAC system, and/or one or more vaporizable and/or non-vaporizable materials. The processor 102 can access a database stored in the memory device 104 to make such a determination or the network device 106 can be used to request information from a server to verify the sensor findings. In an aspect, the server can provide an analysis service to the vapor device 100. For example, the server can analyze data sent by the vapor device 100 based on a reading from the one or more sensors 136. The server can determine and transmit one or more recommendations to the vapor device 100 to mitigate the sensed negative environmental condition. The vapor device 100 can use the one or more recommendations to activate a filtration system, a fan, a fire suppression system engaging a HVAC system, and/or to vaporize one or more vaporizable or non-vaporizable materials to assist in countering effects from the negative environmental condition.

In an aspect, the vapor device 100 can comprise a global positioning system (GPS) unit 118. The GPS 118 can detect a current location of the device 100. In some aspects, a user can request access to one or more services that rely on a current location of the user. For example, the processor 102 can receive location data from the GPS 118, convert it to usable data, and transmit the usable data to the one or more services via the network access device 106. GPS unit 118 can receive position information from a constellation of satellites operated by the U.S. Department of Defense. Alternately, the GPS unit 118 can be a GLONASS receiver operated by the Russian Federation Ministry of Defense, or any other positioning device capable of providing accurate location information (for example, LORAN, inertial navigation, and the like). The GPS unit 118 can contain additional logic, either software, hardware or both to receive the Wide Area Augmentation System (WAAS) signals, operated by the Federal Aviation Administration, to correct dithering errors and provide the most accurate location possible. Overall accuracy of the positioning equipment subsystem containing WAAS is generally in the two meter range.

Figure 2:
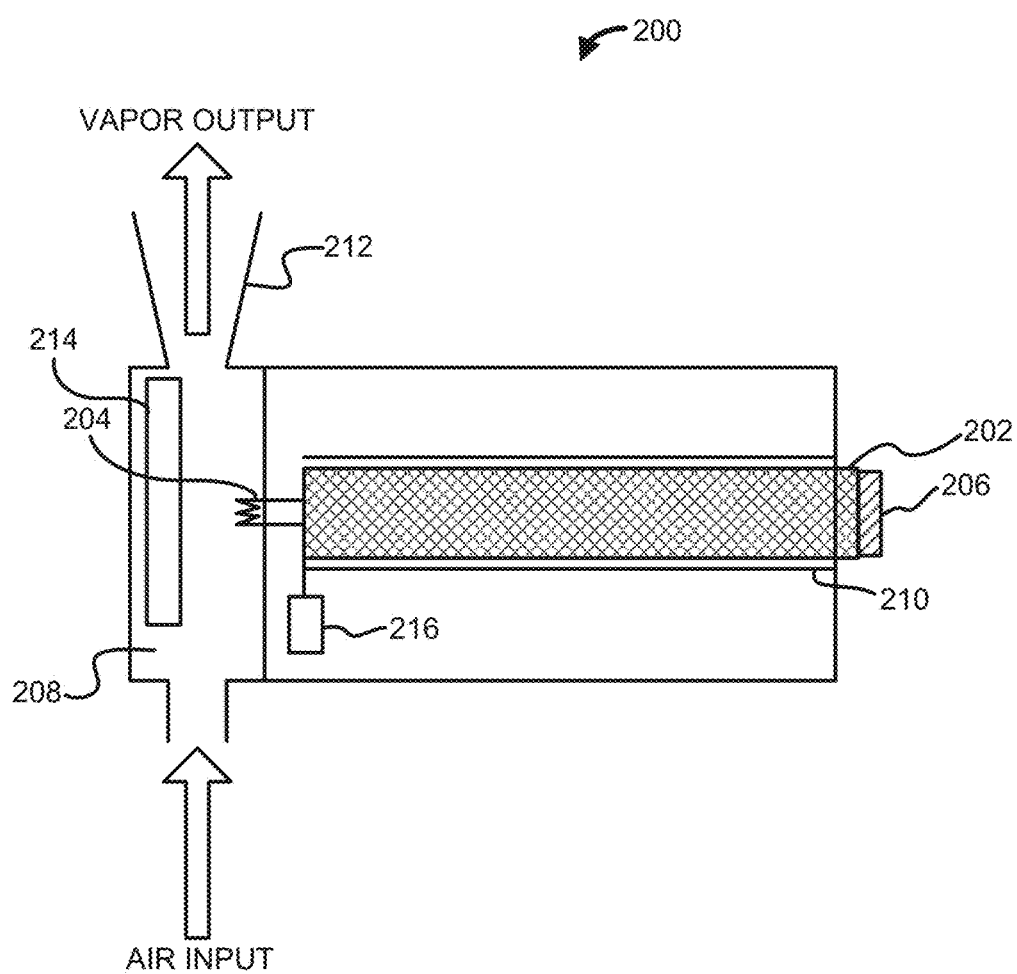
FIG. 2 illustrates an exemplary vaporizer.

FIG. 2 illustrates an exemplary vaporizer 200. The vaporizer 200 can be, for example, an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like. The vaporizer 200 can be used internally of the vapor device 100 or can be a separate device. For example, the vaporizer 200 can be used in place of the vaporizer 108.

The vaporizer 200 can comprise or be coupled to one or more containers 202 containing a vaporizable material, for example a fluid. For example, coupling between the vaporizer 200 and the one or more containers 202 can be via a wick 204, via a valve, or by some other structure. Coupling can operate independently of gravity, such as by capillary action or pressure drop through a valve. The vaporizer 200 can be configured to vaporize the vaporizable material from the one or more containers 202 at controlled rates in response to mechanical input from a component of the vapor device 100, and/or in response to control signals from the processor 102 or another component. Vaporizable material (e.g., fluid) can be supplied by one or more replaceable cartridges 206. In an aspect the vaporizable material can comprise aromatic elements. In an aspect, the aromatic elements can be medicinal, recreational, and/or wellness related. The aromatic element can include, but is not limited to, at least one of lavender or other floral aromatic eLiquids, mint, menthol, herbal soil or geologic, plant based, name brand perfumes, custom mixed perfume formulated inside the vapor device 100 and aromas constructed to replicate the smell of different geographic places, conditions, and/or occurrences. For example, the smell of places may include specific or general sports venues, well known travel destinations, the mix of one's own personal space or home. The smell of conditions may include, for example, the smell of a pet, a baby, a season, a general environment (e.g., a forest), a new car, a sexual nature (e.g., musk, pheromones, etc. . .

.). The one or more replaceable cartridges 206 can contain the vaporizable material. If the vaporizable material is liquid, the cartridge can comprise the wick 204 to aid in transporting the liquid to a mixing chamber 208. In the alternative, some other transport mode can be used. Each of the one or more replaceable cartridges 206 can be configured to fit inside and engage removably with a receptacle (such as the container 202 and/or a secondary container) of the vapor device 100. In an alternative, or in addition, one or more fluid containers 210 can be fixed in the vapor device 100 and configured to be refillable. In an aspect, one or more materials can be vaporized at a single time by the vaporizer 200. For example, some material can be vaporized and drawn through an exhaust port 212 and/or some material can be vaporized and exhausted via a smoke simulator outlet (not shown).

The mixing chamber 208 can also receive an amount of one or more compounds (e.g., vaporizable material) to be vaporized. For example, the processor 102 can determine a first amount of a first compound and determine a second amount of a second compound. The processor 102 can cause the withdrawal of the first amount of the first compound from a first container into the mixing chamber and the second amount of the second compound from a second container into the mixing chamber. The processor 102 can also determine a target dose of the first compound, determine a vaporization ratio of the first compound and the second compound based on the target dose, determine the first amount of the first compound based on the vaporization ratio, determine the second amount of the second compound based on the vaporization ratio, and cause the withdrawal of the first amount of the first compound into the mixing chamber, and the withdrawal of the second amount of the second compound into the mixing chamber.

The processor 102 can also determine a vaporization rate. The vaporization rate can be an amount of vaporizable material vaporized over time. In an aspect, a vaporization rate can be determined a vaporizable material. In another aspect, a vaporization rate can be determined for each of a plurality of vaporizable materials. For example, in an embodiment of the vapor device 100 comprising two different vaporizable materials, each vaporizable material can have a vaporization rate. As a result, both vaporizable materials can be vaporized at the respective vaporization rate and the resulting vapors can be combined. In another aspect, the vaporization rates can be used to determine an amount of each vaporizable material to withdraw into the mixing element 122. The resulting mixture of vaporizable material can then be vaporized. In a further aspect, each container 110 can comprise an independent vaporizer 108 configured to vaporize vaporizable material contained in a corresponding container at a vaporization rate. As a result, the different vaporizable materials can be vaporized independently, yet simultaneously or serially. Vaporization can be performed according to a vaporization rate determined for each vaporizable material.

The processor 102 can also determine a target dose of the first compound, determine a vaporization ratio of the first compound and the second compound based on the target dose, determine the first amount of the first compound based on the vaporization ratio, and determine the second amount of the second compound based on the vaporization ratio. After expelling the vapor through an exhaust port for inhalation by a user, the processor 102 can determine that a cumulative dose is approaching the target dose and reduce the vaporization ratio. In an aspect, one or more of the vaporization ratio, the target dose, and/or the cumulative dose can be determined remotely and transmitted to the vapor device 100 for use.

In operation, a heating element 214 can vaporize or nebulize the vaporizable material in the mixing chamber 208, producing an inhalable vapor/mist that can be expelled via the exhaust port 212. In an aspect, the vaporizer 200 can comprise a plurality of heating elements 214 configured to independently heat different vaporizable materials. In an aspect, the heating element 214 can comprise a heater coupled to the wick (or a heated wick) 204 operatively coupled to (for example, in fluid communication with) the mixing chamber 210. The heating element 214 can comprise a nickel-chromium wire or the like, with a temperature sensor (not shown) such as a thermistor or thermocouple. Within definable limits, by controlling power to the wick 204, a rate of vaporization can be independently controlled. A multiplexer 216 can receive power from any suitable source and exchange data signals with a processor, for example, the processor 102 of the vapor device 100, for control of the vaporizer 200. At a minimum, control can be provided between no power (off state) and one or more powered states. Other control mechanisms can also be suitable.

In another aspect, the vaporizer 200 can comprise a piezoelectric dispersing element. In some aspects, the piezoelectric dispersing element can be charged by a battery, and can be driven by a processor on a circuit board. The circuit board can be produced using a polyimide such as Kapton, or other suitable material. The piezoelectric dispersing element can comprise a thin metal disc which causes dispersion of the fluid fed into the dispersing element via the wick or other soaked piece of organic material through vibration. Once in contact with the piezoelectric dispersing element, the vaporizable material (e.g., fluid) can be vaporized (e.g., turned into vapor or mist) and the vapor can be dispersed via a system pump and/or a sucking action of the user. In some aspects, the piezoelectric dispersing element can cause dispersion of the vaporizable material by producing ultrasonic vibrations. An electric field applied to a piezoelectric material within the piezoelectric element can cause ultrasonic expansion and contraction of the piezoelectric material, resulting in ultrasonic vibrations to the disc. The ultrasonic vibrations can cause the vaporizable material to disperse, thus forming a vapor or mist from the vaporizable material.

In an aspect, the vaporizer 200 can be configured to permit a user to select between using the heating element 214 or the piezoelectric dispersing element. In another aspect, the vaporizer 200 can be configured to permit a user to utilize both the heating element 214 and the piezoelectric dispersing element.

In some aspects, the connection between a power supply and the piezoelectric dispersing element can be facilitated using one or more conductive coils. The conductive coils can provide an ultrasonic power input to the piezoelectric dispersing element. For example, the signal carried by the coil can have a frequency of approximately 107.8 kHz. In some aspects, the piezoelectric dispersing element can comprise a piezoelectric dispersing element that can receive the ultrasonic signal transmitted from the power supply through the coils, and can cause vaporization of the vaporizable liquid by producing ultrasonic vibrations. An ultrasonic electric field applied to a piezoelectric material within the piezoelectric element causes ultrasonic expansion and contraction of the piezoelectric material, resulting in ultrasonic vibrations according to the frequency of the signal. The vaporizable liquid can be vibrated by the ultrasonic energy produced by the piezoelectric dispersing element, thus causing dispersal and/or atomization of the liquid.

Figure 3:
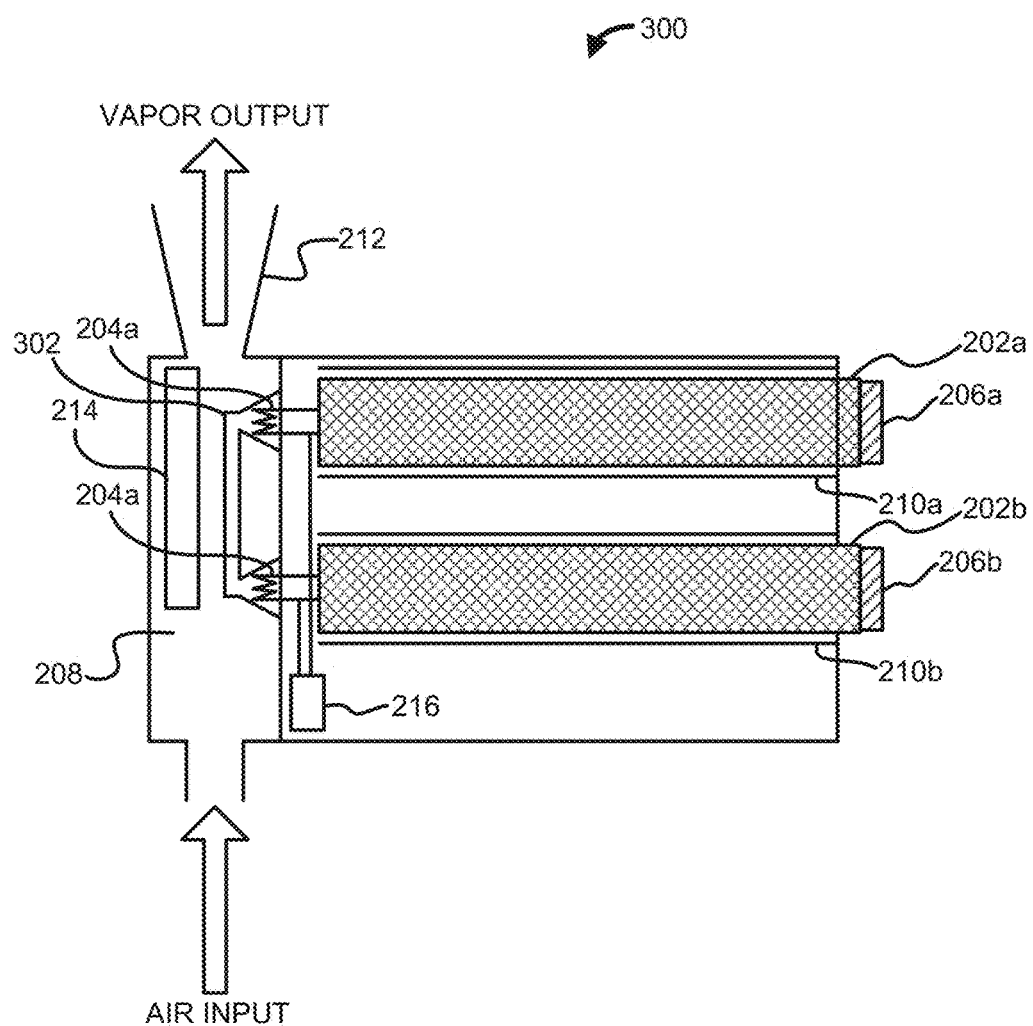
FIG. 3 illustrates an exemplary vaporizer configured for vaporizing a mixture of vaporizable material.

FIG. 3 illustrates a vaporizer 300 that comprises the elements of the vaporizer 200 with two containers 202a and 202b containing a vaporizable material, for example a fluid or a solid. In an aspect, the fluid can be the same fluid in both containers or the fluid can be different in each container. In an aspect the fluid can comprise aromatic elements. The aromatic element can include, but is not limited to, at least one of lavender or other floral aromatic eLiquids, mint, menthol, herbal soil or geologic, plant based, name brand perfumes, custom mixed perfume formulated inside the vapor device 100 and aromas constructed to replicate the smell of different geographic places, conditions, and/or occurrences. For example, the smell of places may include specific or general sports venues, well known travel destinations, the mix of one's own personal space or home. The smell of conditions may include, for example, the smell of a pet, a baby, a season, a general environment (e.g., a forest), a new car, a sexual nature (e.g., musk, pheromones, etc. . . . ). Coupling between the vaporizer 200 and the container 202a and the container 202b can be via a wick 204a and a wick 204b, respectively, via a valve, or by some other structure. Coupling can operate independently of gravity, such as by capillary action or pressure drop through a valve. The vaporizer 300 can be configured to mix in varying proportions the fluids contained in the container 202a and the container 202b and vaporize the mixture at controlled rates in response to mechanical input from a component of the vapor device 100, and/or in response to control signals from the processor 102 or another component. For example, based on a vaporization ratio. In an aspect, a mixing element 302 can be coupled to the container 202a and the container 202b. The mixing element can, in response to a control signal from the processor 102, withdraw select quantities of vaporizable material in order to create a customized mixture of different types of vaporizable material. Vaporizable material (e.g., fluid) can be supplied by one or more replaceable cartridges 206a and 206b. The one or more replaceable cartridges 206a and 206b can contain a vaporizable material. If the vaporizable material is liquid, the cartridge can comprise the wick 204a or 204b to aid in transporting the liquid to a mixing chamber 208. In the alternative, some other transport mode can be used. Each of the one or more replaceable cartridges 206a and 206b can be configured to fit inside and engage removably with a receptacle (such as the container 202a or the container 202b and/or a secondary container) of the vapor device 100. In an alternative, or in addition, one or more fluid containers 210a and 210b can be fixed in the vapor device 100 and configured to be refillable. In an aspect, one or more materials can be vaporized at a single time by the vaporizer 300. For example, some material can be vaporized and drawn through an exhaust port 212 and/or some material can be vaporized and exhausted via a smoke simulator outlet (not shown).

Figure 4:
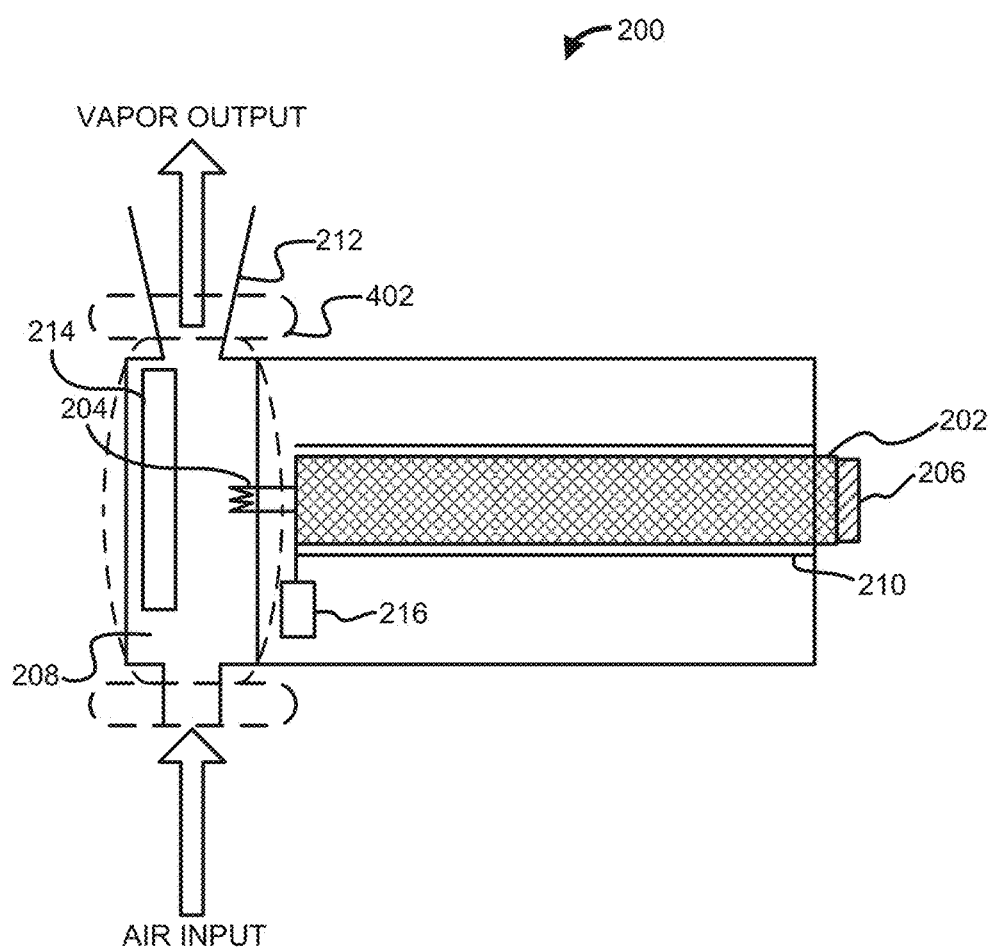
FIG. 4 illustrates an exemplary vaporizer device configured for smooth vapor delivery.

FIG. 4 illustrates a vaporizer 200 that comprises the elements of the vaporizer 200 with a heating casing 402. The heating casing 402 can enclose the heating element 214 or can be adjacent to the heating element 214. The heating casing 402 is illustrated with dashed lines, indicating components contained therein. The heating casing 402 can be made of ceramic, metal, and/or porcelain. The heating casing 402 can have varying thickness. In an aspect, the heating casing 402 can be coupled to the multiplexer 216 to receive power to heat the heating casing 402. In another aspect, the heating casing 402 can be coupled to the heating element 214 to heat the heating casing 402. In another aspect, the heating casing 402 can serve an insulation role.

Figure 5:
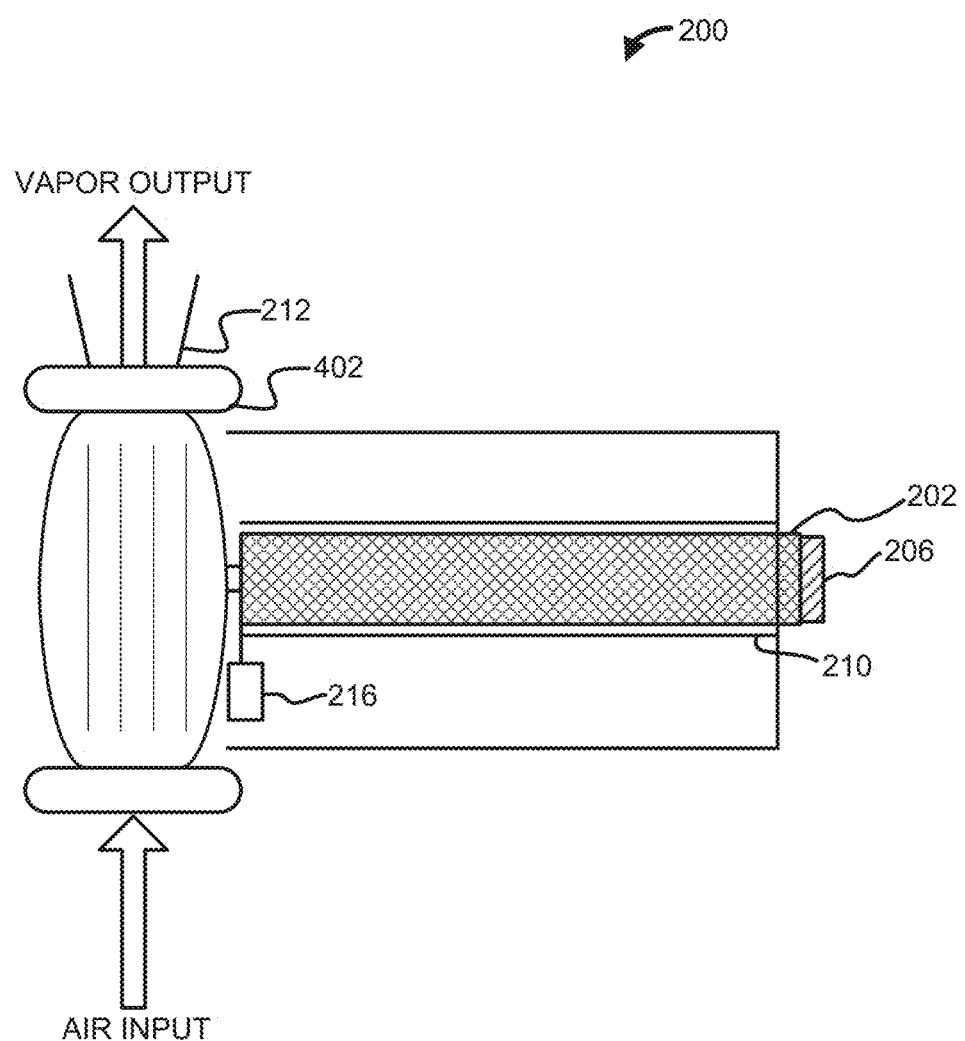
FIG. 5 illustrates another exemplary vaporizer configured for smooth vapor delivery.

FIG. 5 illustrates the vaporizer 200 of FIG. 2 and FIG. 4, but illustrates the heating casing 402 with solid lines, indicating components contained therein. Other placements of the heating casing 402 are contemplated. For example, the heating casing 402 can be placed after the heating element 214 and/or the mixing chamber 208.

Figure 6:
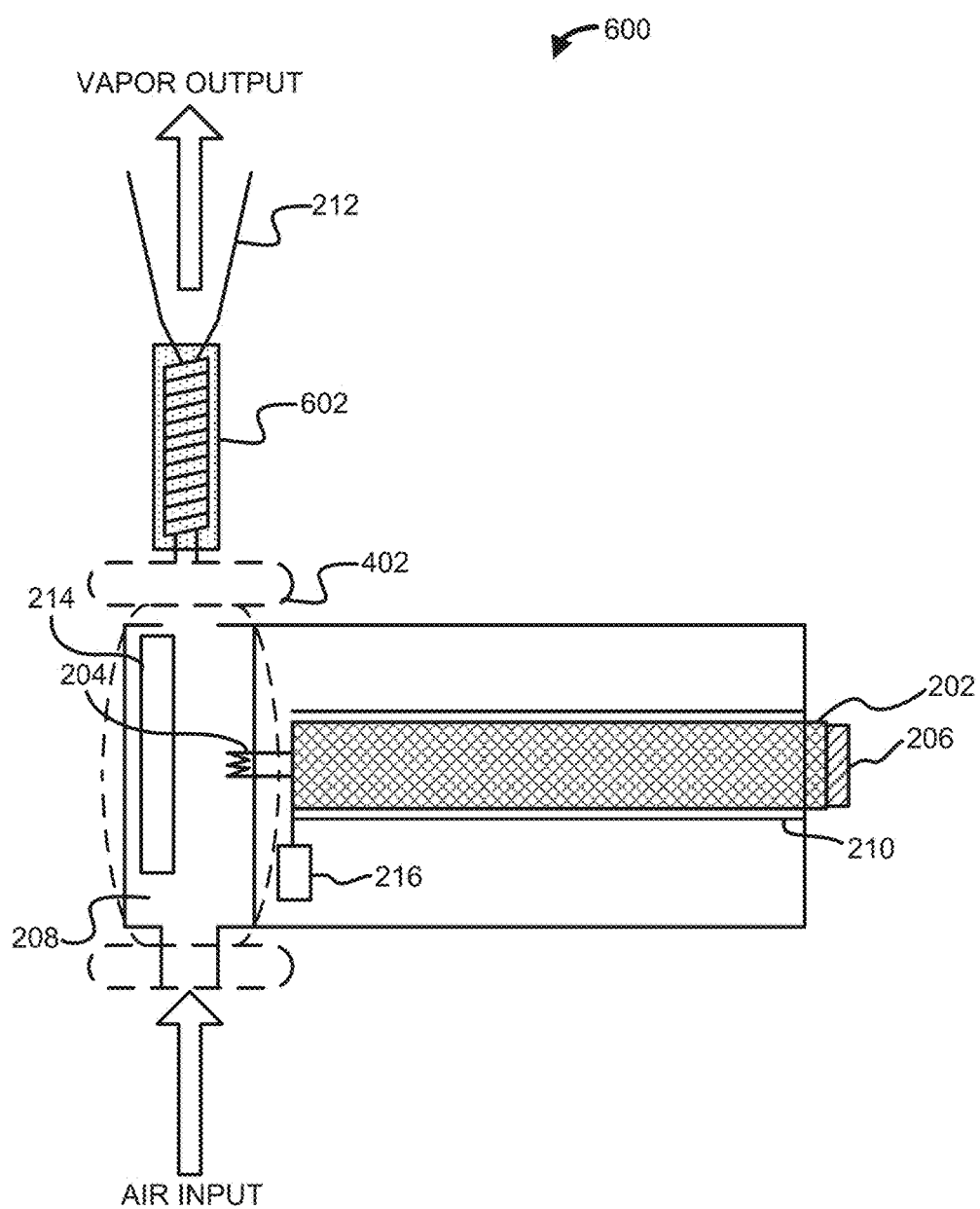
FIG. 6 illustrates another exemplary vaporizer configured for smooth vapor delivery.

FIG. 6 illustrates a vaporizer 600 that comprises the elements of the vaporizer 200 of FIG. 2 and FIG. 4, with the addition of a cooling element 602. The vaporizer 600 can optionally comprise the heating casing 402. The cooling element 602 can comprise one or more of a powered cooling element, a cooling air system, and/or or a cooling fluid system. The cooling element 602 can be self-powered, co-powered, or directly powered by a battery and/or charging system within the vapor device 100 (e.g., the power supply 120). In an aspect, the cooling element 602 can comprise an electrically connected conductive coil, grating, and/or other design to efficiently distribute cooling to the at least one of the vaporized and/or non-vaporized air. For example, the cooling element 602 can be configured to cool air as it is brought into the vaporizer 600/mixing chamber 208 and/or to cool vapor after it exits the mixing chamber 208. The cooling element 602 can be deployed such that the cooling element 602 is surrounded by the heated casing 402 and/or the heating element 214. In another aspect, the heated casing 402 and/or the heating element 214 can be surrounded by the cooling element 602. The cooling element 602 can utilize at least one of cooled air, cooled liquid, and/or cooled matter.

In an aspect, the cooling element 602 can be a coil of any suitable length and can reside proximate to the inhalation point of the vapor (e.g., the exhaust port 212). The temperature of the air is reduced as it travels through the cooling element 602. In an aspect, the cooling element 602 can comprise any structure that accomplishes a cooling effect. For example, the cooling element 602 can be replaced with a screen with a mesh or grid-like structure, a conical structure, and/or a series of cooling airlocks, either stationary or opening, in a periscopic/telescopic manner. The cooling element 602 can be any shape and/or can take multiple forms capable of cooling heated air, which passes through its space.

In an aspect, the cooling element 602 can be any suitable cooling system for use in a vapor device. For example, a fan, a heat sink, a liquid cooling system, a chemical cooling system, combinations thereof, and the like. In an aspect, the cooling element 602 can comprise a liquid cooling system whereby a fluid (e.g., water) passes through pipes in the vaporizer 600. As this fluid passes around the cooling element 602, the fluid absorbs heat, cooling air in the cooling element 602. After the fluid absorbs the heat, the fluid can pass through a heat exchanger which transfers the heat from the fluid to air blowing through the heat exchanger. By way of further example, the cooling element 602 can comprise a chemical cooling system that utilizes an endothermic reaction. An example of an endothermic reaction is dissolving ammonium nitrate in water. Such endothermic process is used in instant cold packs. These cold packs have a strong outer plastic layer that holds a bag of water and a chemical, or mixture of chemicals, that result in an endothermic reaction when dissolved in water. When the cold pack is squeezed, the inner bag of water breaks and the water mixes with the chemicals. The cold pack starts to cool as soon as the inner bag is broken, and stays cold for over an hour. Many instant cold packs contain ammonium nitrate. When ammonium nitrate is dissolved in water, it splits into positive ammonium ions and negative nitrate ions. In the process of dissolving, the water molecules contribute energy, and as a result, the water cools down. Thus, the vaporizer 600 can comprise a chamber for receiving the cooling element 602 in the form of a "cold pack." The cold pack can be activated prior to insertion into the vaporizer 600 or can be activated after insertion through use of a button/switch and the like to mechanically activate the cold pack inside the vaporizer 400.

In an aspect, the cooling element 602 can be selectively moved within the vaporizer 600 to control the temperature of the air mixing with vapor. For example, the cooling element 602 can be moved closer to the exhaust port 212 or further from the exhaust port 212 to regulate temperature. In another aspect, insulation can be incorporated as needed to maintain the integrity of heating and cooling, as well as absorbing any unwanted condensation due to internal or external conditions, or a combination thereof. The insulation can also be selectively moved within the vaporizer 600 to control the temperature of the air mixing with vapor. For example, the insulation can be moved to cover a portion, none, or all of the cooling element 602 to regulate temperature.

Figure 7:
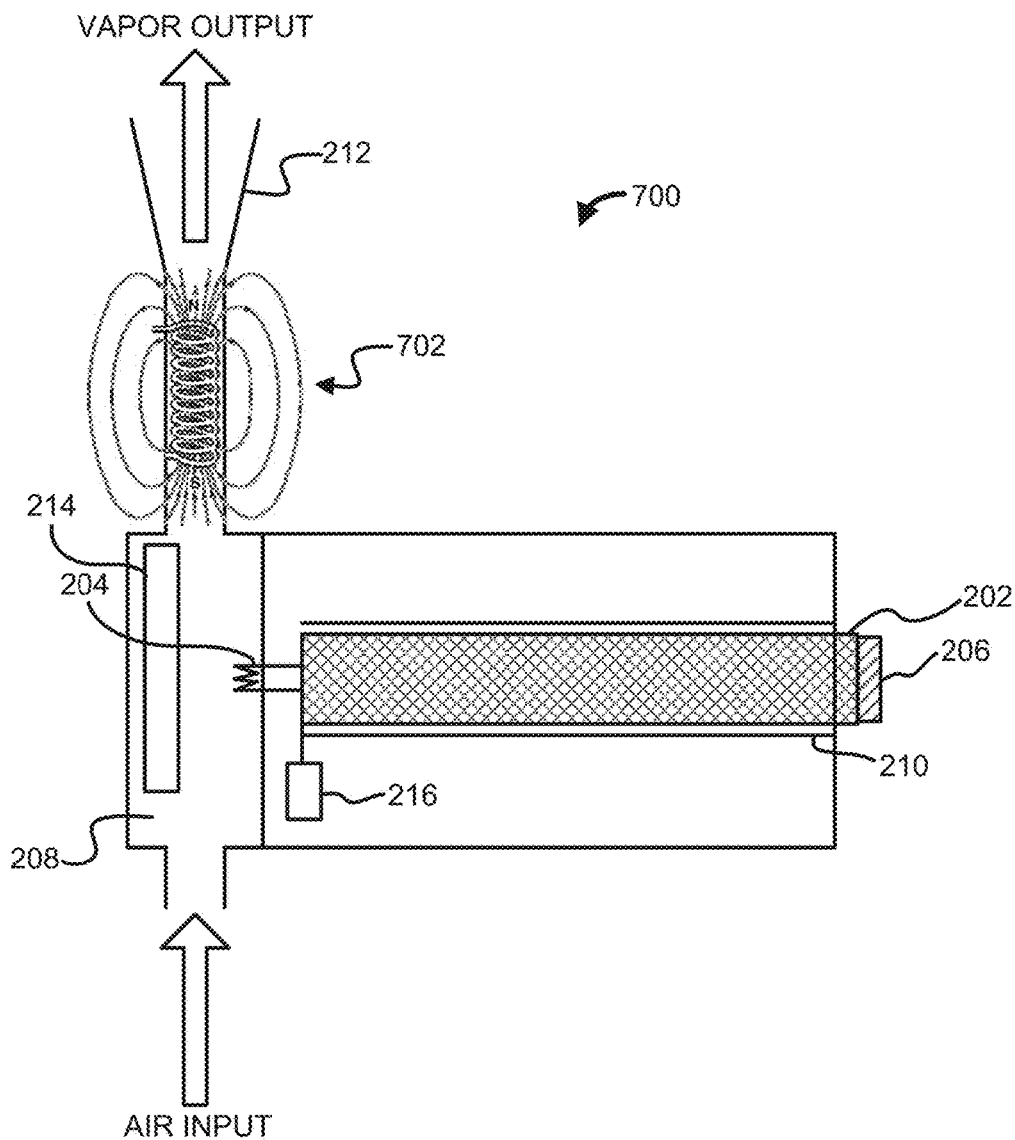
FIG. 7 illustrates another exemplary vaporizer configured for smooth vapor delivery.

FIG. 7 illustrates a vaporizer 700 that comprises elements in common with the vaporizer 200. The vaporizer 700 can optionally comprise the heating casing 402 (not shown) and/or the cooling element 602 (not shown). The vaporizer 700 can comprise a magnetic element 702. The magnetic element 702 can apply a magnetic field to vapor after exiting the mixing chamber 208. The magnetic field can cause positively and negatively charged particles in the vapor to curve in opposite directions, according to the Lorentz force law with two particles of opposite charge. The magnetic field can be created by at least one of an electric current generating a charge or a pre-charged magnetic material deployed within the vapor device 100. In an aspect, the magnetic element 702 can be built into the mixing chamber 208, the cooling element 602, the heating casing 402, or can be a separate magnetic element 702.

Figure 8:
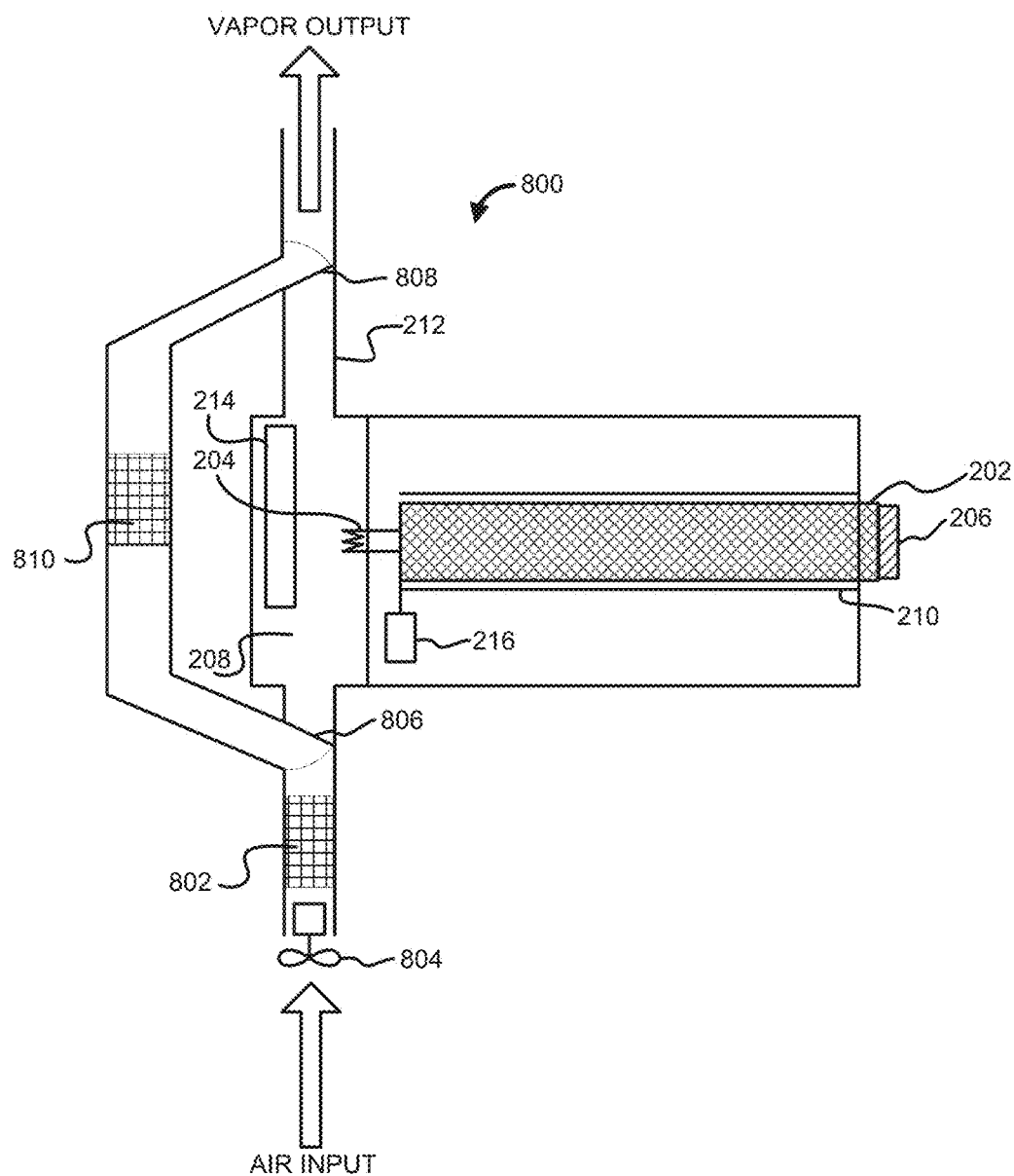
FIG. 8 illustrates an exemplary vaporizer configured for filtering air.

FIG. 8 illustrates a vaporizer 800 that comprises elements in common with the vaporizer 200. In an aspect, the vaporizer 800 can comprise a filtration element 802. The filtration element 802 can be configured to remove (e.g., filter, purify, etc) contaminants from air entering the vaporizer 800. The filtration element 802 can optionally comprise a fan 804 to assist in delivering air to the filtration element 802. The vaporizer 800 can be configured to intake air into the filtration element 802, filter the air, and pass the filtered air to the mixing chamber 208 for use in vaporizing the one or more vaporizable or non-vaporizable materials. In another aspect, the vaporizer 800 can be configured to intake air into the filtration element 802, filter the air, and bypass the mixing chamber 208 by engaging a door 806 and a door 808 to pass the filtered air directly to the exhaust port 212 for inhalation by a user. In an aspect, filtered air that bypasses the mixing chamber 208 by engaging the door 806 and the door 808 can pass through a second filtration element 810 to further remove (e.g., filter, purify, etc) contaminants from air entering the vaporizer 800. In an aspect, the vaporizer 800 can be configured to deploy and/or mix a proper/safe amount of oxygen which can be delivered either via the one or more replaceable cartridges 206 or via air pumped into a mask from external air and filtered through the filtration element 802 and/or the filtration element 810.

In an aspect, the filtration element 802 and/or the filtration element 810 can comprise cotton, polymer, wool, satin, meta materials and the like. The filtration element 802 and/or the filtration element 810 can comprise a filter material that at least one airborne particle and/or undesired gas by a mechanical mechanism, an electrical mechanism, and/or a chemical mechanism. The filter material can comprise one or more pieces of, a filter fabric that can filter out one or more airborne particles and/or gasses. The filter fabric can be a woven and/or non-woven material. The filter fabric can be made from natural fibers (e.g., cotton, wool, etc.) and/or from synthetic fibers (e.g., polyester, nylon, polypropylene, etc.). The thickness of the filter fabric can be varied depending on the desired filter efficiencies and/or the region of the apparel where the filter fabric is to be used. The filter fabric can be designed to filter airborne particles and/or gasses by mechanical mechanisms (e.g., weave density), by electrical mechanisms (e.g., charged fibers, charged metals, etc.), and/or by chemical mechanisms (e.g., absorptive charcoal particles, adsorptive materials, etc.). In as aspect, the filter material can comprise electrically charged fibers such as, but not limited to, FILTRETE by 3M. In another aspect, the filter material can comprise a high density material similar to material used for medical masks which are used by medical personnel in doctors' offices, hospitals, and the like. In an aspect, the filter material can be treated with an anti-bacterial solution and/or otherwise made from anti-bacterial materials. In another aspect, the filtration element 802 and/or the filtration element 810 can comprise electrostatic plates, ultraviolet light, a HEPA filter, combinations thereof, and the like.

Figure 9:
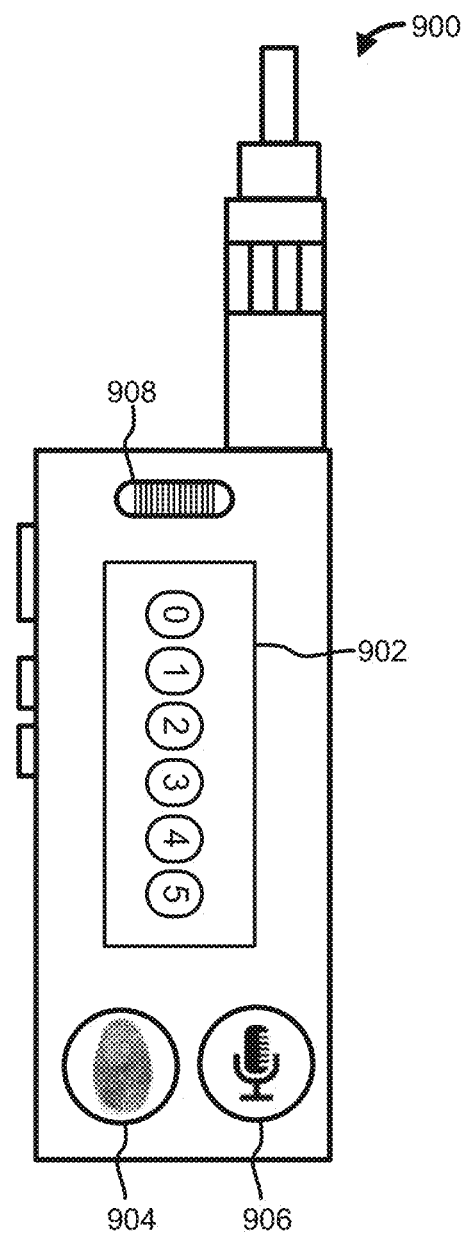
FIG. 9 illustrates an interface of an exemplary electronic vapor device.

FIG. 9 illustrates an exemplary vapor device 900. The exemplary vapor device 900 can comprise the vapor device 100 and/or any of the vaporizers disclosed herein. The exemplary vapor device 900 illustrates a display 902. The display 902 can be a touchscreen. The display 902 can be configured to enable a user to control any and/or all functionality of the exemplary vapor device 900. For example, a user can utilize the display 902 to enter a pass code to lock and/or unlock the exemplary vapor device 900. The exemplary vapor device 900 can comprise a biometric interface 904. For example, the biometric interface 904 can comprise a fingerprint scanner, an eye scanner, a facial scanner, and the like. The biometric interface 904 can be configured to enable a user to control any and/or all functionality of the exemplary vapor device 900. The exemplary vapor device 900 can comprise an audio interface 906. The audio interface 906 can comprise a button that, when engaged, enables a microphone 908. The microphone 908 can receive audio signals and provide the audio signals to a processor for interpretation into one or more commands to control one or more functions of the exemplary vapor device 900.

Figure 10:
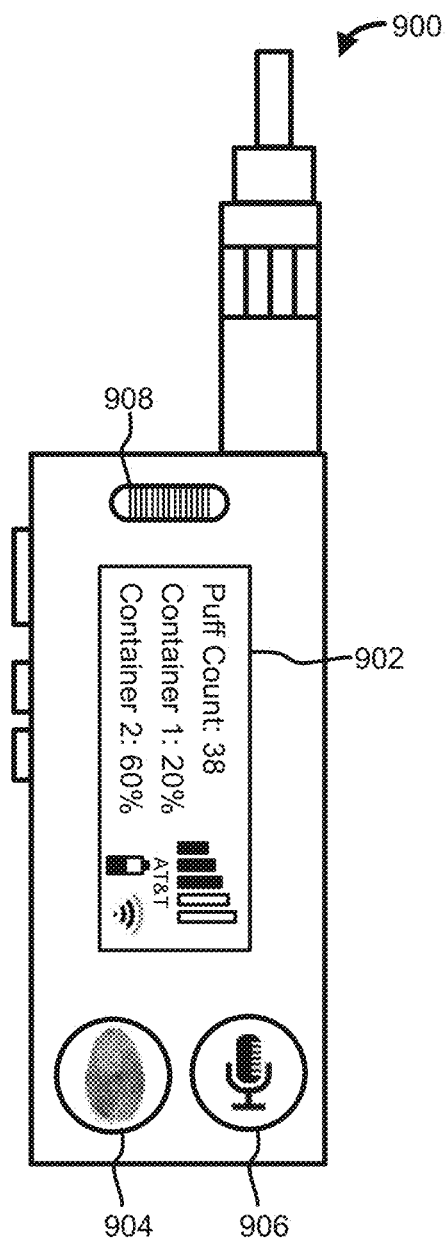
FIG. 10 illustrates another interface of an exemplary electronic vapor device.

FIG. 10 illustrates exemplary information that can be provided to a user via the display 902 of the exemplary vapor device 900. The display 902 can provide information to a user such as a puff count, an amount of vaporizable material remaining in one or more containers, battery remaining, signal strength, combinations thereof, and the like.

Figure 11:
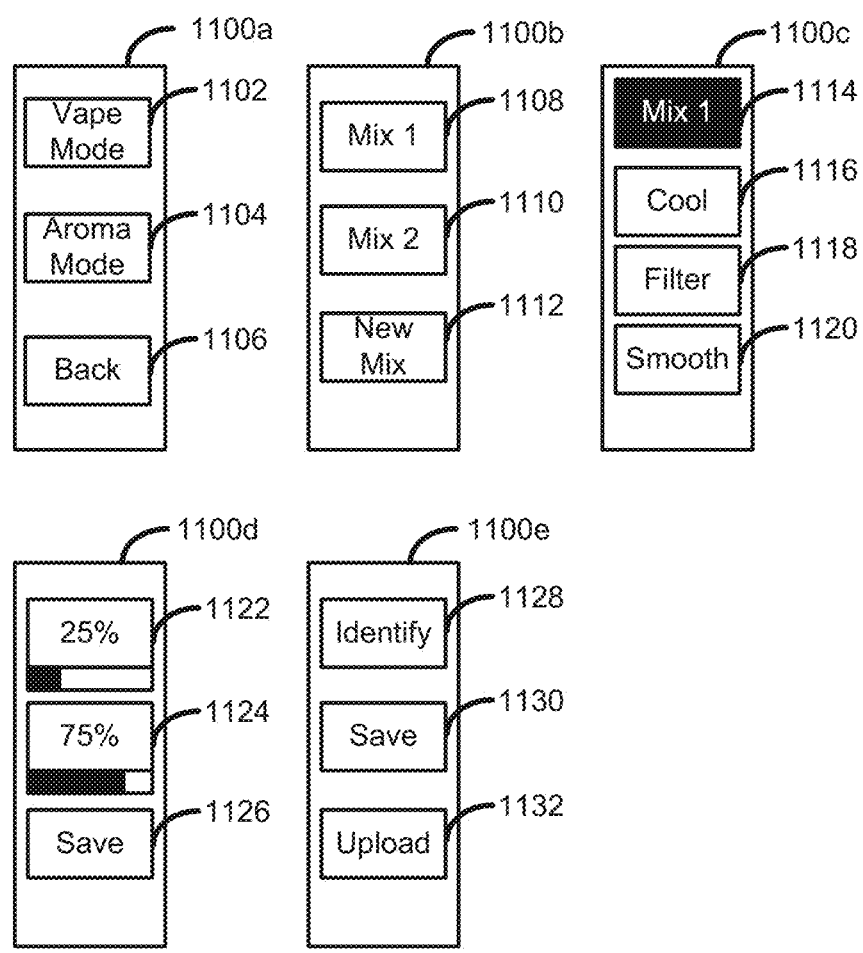
FIG. 11 illustrates several interfaces of an exemplary electronic vapor device.

FIG. 11 illustrates a series of user interfaces that can be provided via the display 902 of the exemplary vapor device 900. In an aspect, the exemplary vapor device 900 can be configured for one or more of multi-mode vapor usage. For example, the exemplary vapor device 900 can be configured to enable a user to inhale vapor (vape mode) or to release vapor into the atmosphere (aroma mode). User interface 1100a provides a user with interface elements to select which mode the user wishes to engage, a Vape Mode 1102, an Aroma Mode 1104, or an option to go back 1106 and return to the previous screen. The interface element Vape Mode 1102 enables a user to engage a vaporizer to generate a vapor for inhalation. The interface element Aroma Mode 1104 enables a user to engage the vaporizer to generate a vapor for release into the atmosphere.

In the event a user selects the Vape Mode 1102, the exemplary vapor device 900 will be configured to vaporize material and provide the resulting vapor to the user for inhalation. The user can be presented with user interface 1100b which provides the user an option to select interface elements that will determine which vaporizable material to vaporize. For example, an option of Mix 1 1108, Mix 2 1110, or a New Mix 1112. The interface element Mix 1 1108 enables a user to engage one or more containers that contain vaporizable material in a predefined amount and/or ratio. In an aspect, a selection of Mix 1 1108 can result in the exemplary vapor device 900 engaging a single container containing a single type of vaporizable material or engaging a plurality of containers containing a different types of vaporizable material in varying amounts. The interface element Mix 2 1110 enables a user to engage one or more containers that contain vaporizable material in a predefined amount and/or ratio. In an aspect, a selection of Mix 2 1110 can result in the exemplary vapor device 900 engaging a single container containing a single type of vaporizable material or engaging a plurality of containers containing a different types of vaporizable material in varying amounts. In an aspect, a selection of New Mix 1112 can result in the exemplary vapor device 900 receiving a new mixture, formula, recipe, etc. . . . of vaporizable materials and/or engage one or more containers that contain vaporizable material in the new mixture.

Upon selecting, for example, the Mix 1 1108, the user can be presented with user interface 1100c. User interface 1100c indicates to the user that Mix 1 has been selected via an indicator 1114. The user can be presented with options that control how the user wishes to experience the selected vapor. The user can be presented with interface elements Cool 1116, Filter 1118, and Smooth 1120. The interface element Cool 1116 enables a user to engage one or more cooling elements to reduce the temperature of the vapor. The interface element Filter 1118 enables a user to engage one or more filter elements to filter the air used in the vaporization process. The interface element Smooth 1120 enables a user to engage one or more heating casings, cooling elements, filter elements, and/or magnetic elements to provide the user with a smoother vaping experience.

Upon selecting New Mix 1112, the user can be presented with user interface 1100d. User interface 1100d provides the user with a container one ratio interface element 1122, a container two ratio interface element 1124, and Save 1126. The container one ratio interface element 1122 and the container two ratio interface element 1124 provide a user the ability to select an amount of each type of vaporizable material contained in container one and/or container two to utilize as a new mix. The container one ratio interface element 1122 and the container two ratio interface element 1124 can provide a user with a slider that adjusts the percentages of each type of vaporizable material based on the user dragging the slider. In an aspect, a mix can comprise 100% on one type of vaporizable material or any percent combination (e.g., 50/50, 75/25, 85/15, 95/5, etc. . . . ). Once the user is satisfied with the new mix, the user can select Save 1126 to save the new mix for later use.

In the event a user selects the Aroma Mode 1104, the exemplary vapor device 900 will be configured to vaporize material and release the resulting vapor into the atmosphere. The user can be presented with user interface 1100b, 1100c, and/or 1100d as described above, but the resulting vapor will be released to the atmosphere.

In an aspect, the user can be presented with user interface 1100e. The user interface 1100e can provide the user with interface elements Identify 1128, Save 1130, and Upload 1132. The interface element Identify 1128 enables a user to engage one or more sensors in the exemplary vapor device 900 to analyze the surrounding environment. For example, activating the interface element Identify 1128 can engage a sensor to determine the presence of a negative environmental condition such as smoke, a bad smell, chemicals, etc. Activating the interface element Identify 1128 can engage a sensor to determine the presence of a positive environmental condition, for example, an aroma. The interface element Save 1130 enables a user to save data related to the analyzed negative and/or positive environmental condition in memory local to the exemplary vapor device 900. The interface element Upload 1132 enables a user to engage a network access device to transmit data related to the analyzed negative and/or positive environmental condition to a remote server for storage and/or analysis.

Figure 12:
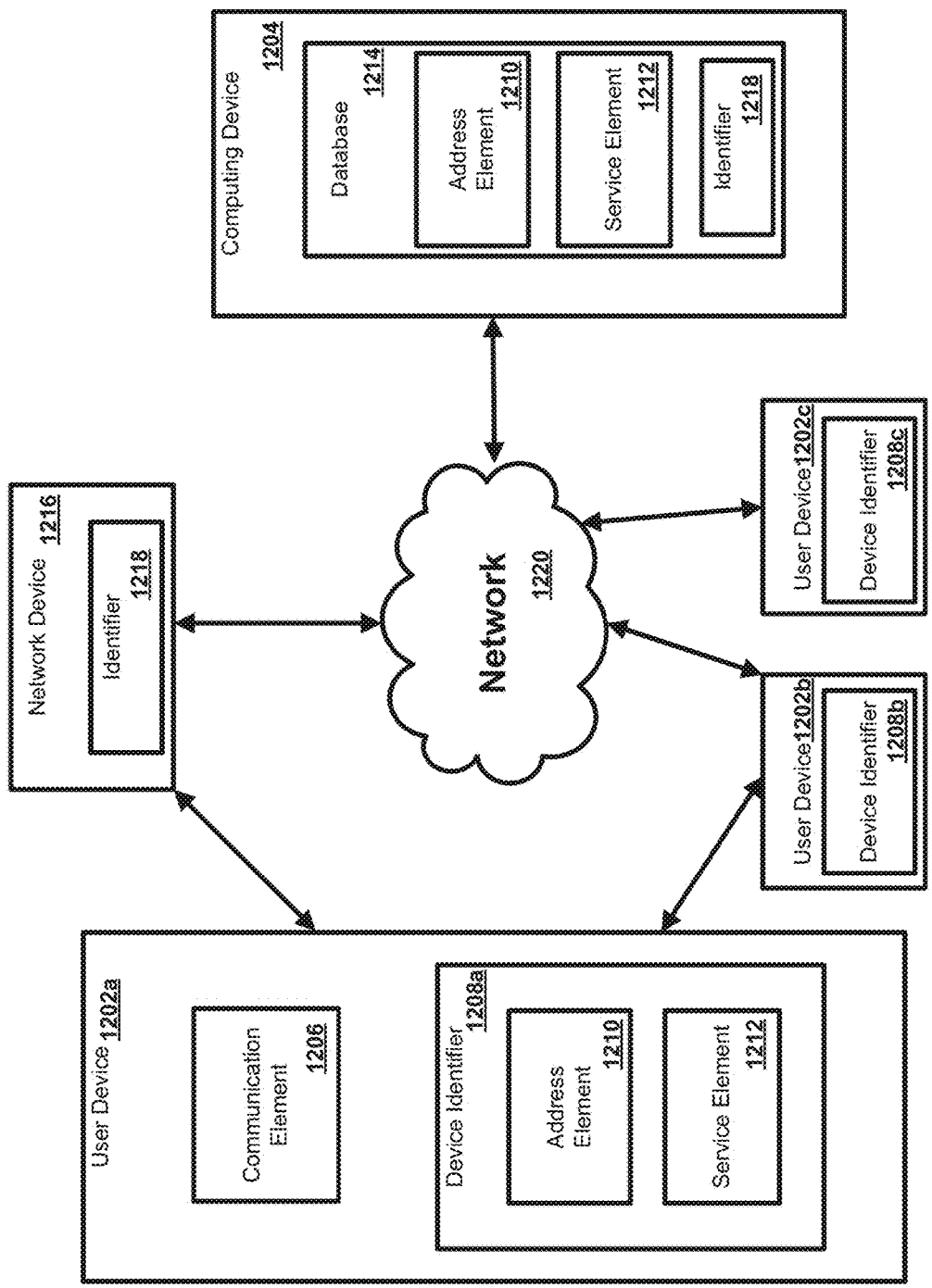
FIG. 12 illustrates an exemplary operating environment.

In one aspect of the disclosure, a system can be configured to provide services such as network-related services to a user device. FIG. 12 illustrates various aspects of an exemplary environment in which the present methods and systems can operate. The present disclosure is relevant to systems and methods for providing services to a user device, for example, electronic vapor devices which can include, but are not limited to, a vape-bot, micro-vapor device, vapor pipe, e-cigarette, hybrid handset and vapor device, and the like. Other user devices that can be used in the systems and methods include, but are not limited to, a smart watch (and any other form of "smart" wearable technology), a smartphone, a tablet, a laptop, a desktop, and the like. In an aspect, one or more network devices can be configured to provide various services to one or more devices, such as devices located at or near a premises. In another aspect, the network devices can be configured to recognize an authoritative device for the premises and/or a particular service or services available at the premises. As an example, an authoritative device can be configured to govern or enable connectivity to a network such as the Internet or other remote resources, provide address and/or configuration services like DHCP, and/or provide naming or service discovery services for a premises, or a combination thereof. Those skilled in the art will appreciate that present methods can be used in various types of networks and systems that employ both digital and analog equipment. One skilled in the art will appreciate that provided herein is a functional description and that the respective functions can be performed by software, hardware, or a combination of software and hardware.

The network and system can comprise a user device 1202a, 1202b, and/or 1202c in communication with a computing device 1204 such as a server, for example. The computing device 1204 can be disposed locally or remotely relative to the user device 1202a, 1202b, and/or 1202c. As an example, the user device 1202a, 1202b, and/or 1202c and the computing device 1204 can be in communication via a private and/or public network 1220 such as the Internet or a local area network. Other forms of communications can be used such as wired and wireless telecommunication channels, for example. In another aspect, the user device 1202a, 1202b, and/or 1202c can communicate directly without the use of the network 1220 (for example, via Bluetooth®, infrared, and the like).

In an aspect, the user device 1202a, 1202b, and/or 1202c can be an electronic device such as an electronic vapor device (e.g., vape-bot, micro-vapor device, vapor pipe, e-cigarette, hybrid handset and vapor device), a smartphone, a smart watch, a computer, a smartphone, a laptop, a tablet, a set top box, a display device, or other device capable of communicating with the computing device 1204. As an example, the user device 1202a, 1202b, and/or 1202c can comprise a communication element 1206 for providing an interface to a user to interact with the user device 1202a, 1202b, and/or 1202c and/or the computing device 1204. The communication element 1206 can be any interface for presenting and/or receiving information to/from the user, such as user feedback. An example interface can be communication interface such as a web browser (e.g., Internet Explorer, Mozilla Firefox, Google Chrome, Safari, or the like). Other software, hardware, and/or interfaces can be used to provide communication between the user and one or more of the user device 1202a, 1202b, and/or 1202c and the computing device 1204. In an aspect, the user device 1202a, 1202b, and/or 1202c can have at least one similar interface quality such as a symbol, a voice activation protocol, a graphical coherence, a startup sequence continuity element of sound, light, vibration or symbol. In an aspect, the interface can comprise at least one of lighted signal lights, gauges, boxes, forms, words, video, audio scrolling, user selection systems, vibrations, check marks, avatars, matrix', visual images, graphic designs, lists, active calibrations or calculations, 2D interactive fractal designs, 3D fractal designs, 2D and/or 3D representations of vapor devices and other interface system functions.

As an example, the communication element 1206 can request or query various files from a local source and/or a remote source. As a further example, the communication element 1206 can transmit data to a local or remote device such as the computing device 1204. In an aspect, data can be shared anonymously with the computing device 1204. The data can be shared over a transient data session with the computing device 1204. The transient data session can comprise a session limit. The session limit can be based on one or more of a number of puffs, a time limit, and a total quantity of vaporizable material. The data can comprise usage data and/or a usage profile. The computing device 1204 can destroy the data once the session limit is reached.

In an aspect, the user device 1202a, 1202b, and/or 1202c can be associated with a user identifier or device identifier 1208a, 1208b, and/or 1208c. As an example, the device identifier 1208a, 1208b, and/or 1208c can be any identifier, token, character, string, or the like, for differentiating one user or user device (e.g., user device 1202a, 1202b, and/or 1202c) from another user or user device. In a further aspect, the device identifier 1208a, 1208b, and/or 1208c can identify a user or user device as belonging to a particular class of users or user devices. As a further example, the device identifier 1208a, 1208b, and/or 1208c can comprise information relating to the user device such as a manufacturer, a model or type of device, a service provider associated with the user device 1202a, 1202b, and/or 1202c, a state of the user device 1202a, 1202b, and/or 1202c, a locator, and/or a label or classifier. Other information can be represented by the device identifier 1208a, 1208b, and/or 1208c.

In an aspect, the device identifier 1208a, 1208b, and/or 1208c can comprise an address element 1210 and a service element 1212. In an aspect, the address element 1210 can comprise or provide an internet protocol address, a network address, a media access control (MAC) address, an Internet address, or the like. As an example, the address element 1210 can be relied upon to establish a communication session between the user device 1202a, 1202b, and/or 1202c and the computing device 1204 or other devices and/or networks. As a further example, the address element 1210 can be used as an identifier or locator of the user device 1202a, 1202b, and/or 1202c. In an aspect, the address element 1210 can be persistent for a particular network.

In an aspect, the service element 1212 can comprise an identification of a service provider associated with the user device 1202a, 1202b, and/or 1202c and/or with the class of user device 1202a, 1202b, and/or 1202c. The class of the user device 1202a, 1202b, and/or 1202c can be related to a type of device, capability of device, type of service being provided, and/or a level of service. As an example, the service element 1212 can comprise information relating to or provided by a communication service provider (e.g., Internet service provider) that is providing or enabling data flow such as communication services to and/or between the user device 1202a, 1202b, and/or 1202c. As a further example, the service element 1212 can comprise information relating to a preferred service provider for one or more particular services relating to the user device 1202a, 1202b, and/or 1202c. In an aspect, the address element 1210 can be used to identify or retrieve data from the service element 1212, or vice versa. As a further example, one or more of the address element 1210 and the service element 1212 can be stored remotely from the user device 1202a, 1202b, and/or 1202c and retrieved by one or more devices such as the user device 1202a, 1202b, and/or 1202c and the computing device 1204. Other information can be represented by the service element 1212.

In an aspect, the computing device 1204 can be a server for communicating with the user device 1202a, 1202b, and/or 1202c. As an example, the computing device 1204 can communicate with the user device 1202a, 1202b, and/or 1202c for providing data and/or services. As an example, the computing device 1204 can provide services such as data sharing, data syncing, network (e.g., Internet) connectivity, network printing, media management (e.g., media server), content services, streaming services, broadband services, or other network-related services. In an aspect, the computing device 1204 can allow the user device 1202a, 1202b, and/or 1202c to interact with remote resources such as data, devices, and files. As an example, the computing device can be configured as (or disposed at) a central location, which can receive content (e.g., data) from multiple sources, for example, user devices 1202a, 1202b, and/or 1202c. The computing device 1204 can combine the content from the multiple sources and can distribute the content to user (e.g., subscriber) locations via a distribution system.

In an aspect, one or more network devices 1216 can be in communication with a network such as network 1220. As an example, one or more of the network devices 1216 can facilitate the connection of a device, such as user device 1202a, 1202b, and/or 1202c, to the network 1220. As a further example, one or more of the network devices 1216 can be configured as a wireless access point (WAP). In an aspect, one or more network devices 1216 can be configured to allow one or more wireless devices to connect to a wired and/or wireless network using Wi-Fi, Bluetooth or any desired method or standard.

In an aspect, the network devices 1216 can be configured as a local area network (LAN). As an example, one or more network devices 1216 can comprise a dual band wireless access point. As an example, the network devices 1216 can be configured with a first service set identifier (SSID) (e.g., associated with a user network or private network) to function as a local network for a particular user or users. As a further example, the network devices 1216 can be configured with a second service set identifier (SSID) (e.g., associated with a public/community network or a hidden network) to function as a secondary network or redundant network for connected communication devices.

In an aspect, one or more network devices 1216 can comprise an identifier 1218. As an example, one or more identifiers can be or relate to an Internet Protocol (IP) Address IPV4/IPV6 or a media access control address (MAC address) or the like. As a further example, one or more identifiers 1218 can be a unique identifier for facilitating communications on the physical network segment. In an aspect, each of the network devices 1216 can comprise a distinct identifier 1218. As an example, the identifiers 1218 can be associated with a physical location of the network devices 1216.

In an aspect, the computing device 1204 can manage the communication between the user device 1202*a*, 1202*b*, and/or 1202*c* and a database 1214 for sending and receiving data therebetween. As an example, the database 1214 can store a plurality of files (e.g., web pages), user identifiers or records, or other information. In one aspect, the database 1214 can store user device 1202*a*, 1202*b*, and/or 1202*c* usage information (including chronological usage), type of vaporizable and/or non-vaporizable material used, frequency of usage, location of usage, recommendations, communications (e.g., text messages, advertisements, photo messages), simultaneous use of multiple devices, and the like). The database 1214 can collect and store data to support cohesive use, wherein cohesive use is indicative of the use of a first electronic vapor devices and then a second electronic vapor device is synced chronologically and logically to provide the proper specific properties and amount of vapor based upon a designed usage cycle. As a further example, the user device 1202*a*, 1202*b*, and/or 1202*c* can request and/or retrieve a file from the database 1214. The user device 1202*a*, 1202*b*, and/or 1202*c* can thus sync locally stored data with more current data available from the database 1214. Such syncing can be set to occur automatically on a set time schedule, on demand, and/or in real-time. The computing device 1204 can be configured to control syncing functionality. For example, a user can select one or more of the user device 1202*a*, 1202*b*, and/or 1202*c* to never by synced, to be the master data source for syncing, and the like. Such functionality can be configured to be controlled by a master user and any other user authorized by the master user or agreement.

In an aspect, data can be derived by system and/or device analysis. Such analysis can comprise at least by one of instant analysis performed by the user device 1202*a*, 1202*b*, and/or 1202*c* or archival data transmitted to a third party for analysis and returned to the user device 1202*a*, 1202*b*, and/or 1202*c* and/or computing device 1204. The result of either data analysis can be communicated to a user of the user device 1202*a*, 1202*b*, and/or 1202*c* to, for example, inform the user of their eVapor use and/or lifestyle options. In an aspect, a result can be transmitted back to at least one authorized user interface.

In an aspect, the database 1214 can store information relating to the user device 1202*a*, 1202*b*, and/or 1202*c* such as the address element 1210 and/or the service element 1212. As an example, the computing device 1204 can obtain the device identifier 1208*a*, 1208*b*, and/or 1208*c* from the user device 1202*a*, 1202*b*, and/or 1202*c* and retrieve information from the database 1214 such as the address element 1210 and/or the service elements 1212. As a further example, the computing device 1204 can obtain the address element 1210 from the user device 1202*a*, 1202*b*, and/or 1202*c* and can retrieve the service element 1212 from the database 1214, or vice versa. Any information can be stored in and retrieved from the database 1214. The database 1214 can be disposed remotely from the computing device 1204 and accessed via direct or indirect connection. The database 1214 can be integrated with the computing device 1204 or some other device or system. Data stored in the database 1214 can be stored anonymously and can be destroyed based on a transient data session reaching a session limit.

Figure 13:
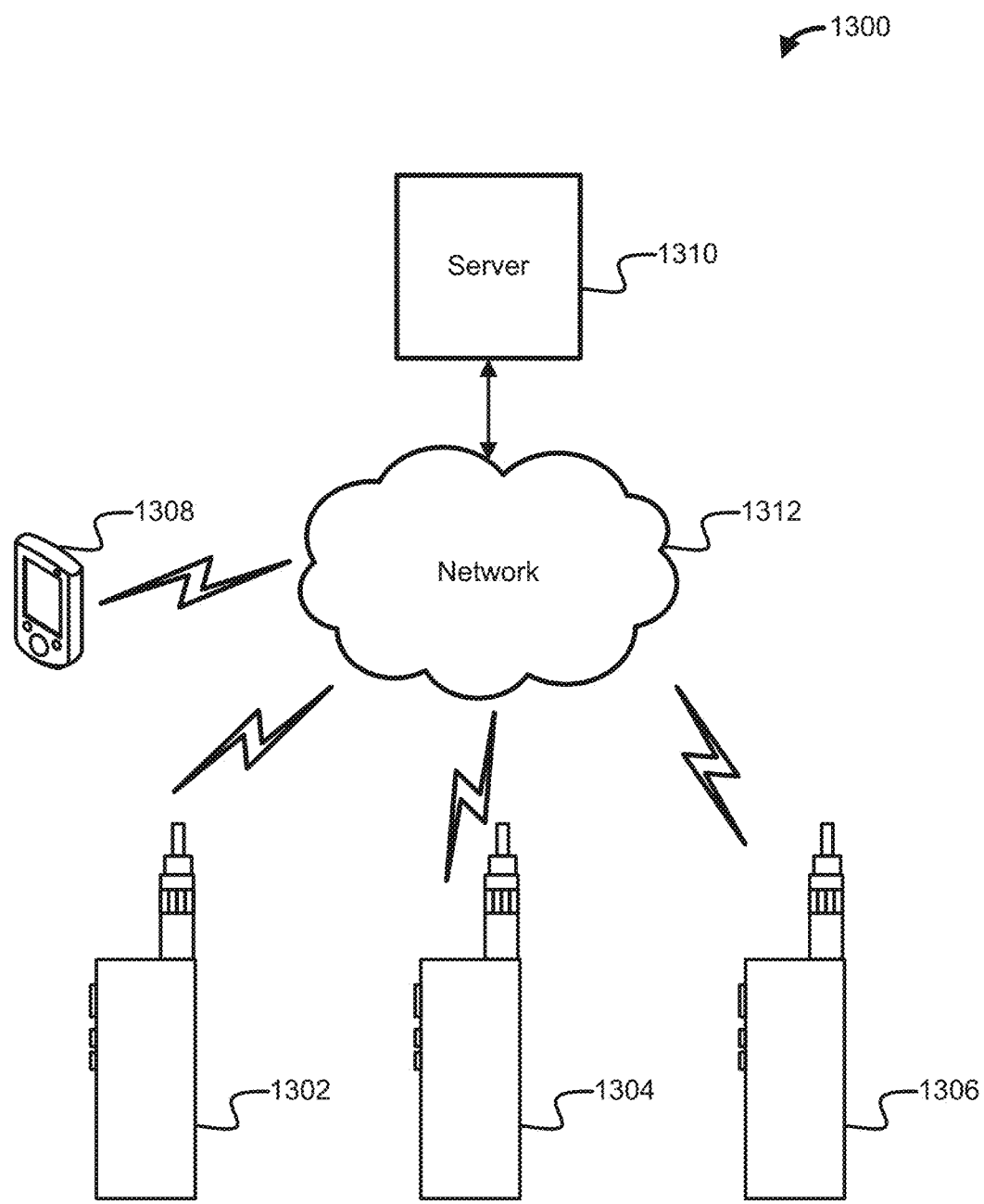
FIG. 13 illustrates another exemplary operating environment.

FIG. 13 illustrates an ecosystem 1300 configured for sharing and/or syncing data such as usage information (including chronological usage), type of vaporizable and/or non-vaporizable material used, frequency of usage, location of usage, recommendations, communications (e.g., text messages, advertisements, photo messages), simultaneous use of multiple devices, and the like) between one or more devices such as a vapor device 1302, a vapor device 1304, a vapor device 1306, and an electronic communication device 1308. In an aspect, the vapor device 1302, the vapor device 1304, the vapor device 1306 can be one or more of an e-cigarette, an e-cigar, an electronic vapor modified device, a hybrid electronic communication handset coupled/integrated vapor device, a micro-sized electronic vapor device, or a robotic vapor device. In an aspect, the electronic communication device 1308 can comprise one or more of a smartphone, a smart watch, a tablet, a laptop, and the like.

In an aspect data generated, gathered, created, etc., by one or more of the vapor device 1302, the vapor device 1304, the vapor device 1306, and/or the electronic communication device 1308 can be uploaded to and/or downloaded from a central server 1310 via a network 1312, such as the Internet. Such uploading and/or downloading can be performed via any form of communication including wired and/or wireless. In an aspect, the vapor device 1302, the vapor device 1304, the vapor device 1306, and/or the electronic communication device 1308 can be configured to communicate via cellular communication, WiFi communication, Bluetooth® communication, satellite communication, and the like. The central server 1310 can store uploaded data and associate the uploaded data with a user and/or device that uploaded the data. The central server 1310 can access unified account and tracking information to determine devices that are associated with each other, for example devices that are owned/used by the same user. The central server 1310 can utilize the unified account and tracking information to determine which of the vapor device 1302, the vapor device 1304, the vapor device 1306, and/or the electronic communication device 1308, if any, should receive data uploaded to the central server 1310.

In an aspect, the uploading and downloading can be performed anonymously. The data can be shared over a transient data session with the central server 1310. The transient data session can comprise a session limit. The session limit can be based on one or more of a number of puffs, a time limit, and a total quantity of vaporizable material. The data can comprise usage data and/or a usage profile. The central server 1310 can destroy the data once the session limit is reached. While the transient data session is active, the central server 1310 can provide a usage profile to one of the vapor device 1302, the vapor device 1304, the vapor device 1306 to control the functionality for the duration of the transient data session.

For example, the vapor device 1302 can be configured to upload usage information related to vaporizable material consumed and the electronic communication device 1308 can be configured to upload location information related to location of the vapor device 1302. The central server 1310 can receive both the usage information and the location information, access the unified account and tracking information to determine that both the vapor device 1302 and the electronic communication device 1308 are associated with the same user. The central server 1310 can thus correlate the user's location along with the type, amount, and/or timing of usage of the vaporizable material. The central server 1310 can further determine which of the other devices are permitted to receive such information and transmit the information based on the determined permissions. In an aspect, the central server 1310 can transmit the correlated information to the electronic communication device 1308 which can then subsequently use the correlated information to recommend a specific type of vaporizable material to the user when the user is located in the same geographic position indicated by the location information.

In another aspect, the central server 1310 can provide one or more social networking services for users of the vapor device 1302, the vapor device 1304, the vapor device 1306, and/or the electronic communication device 1308. Such social networking services include, but are not limited to, messaging (e.g., text, image, and/or video), mixture sharing, product recommendations, location sharing, product ordering, and the like.

Figure 14:
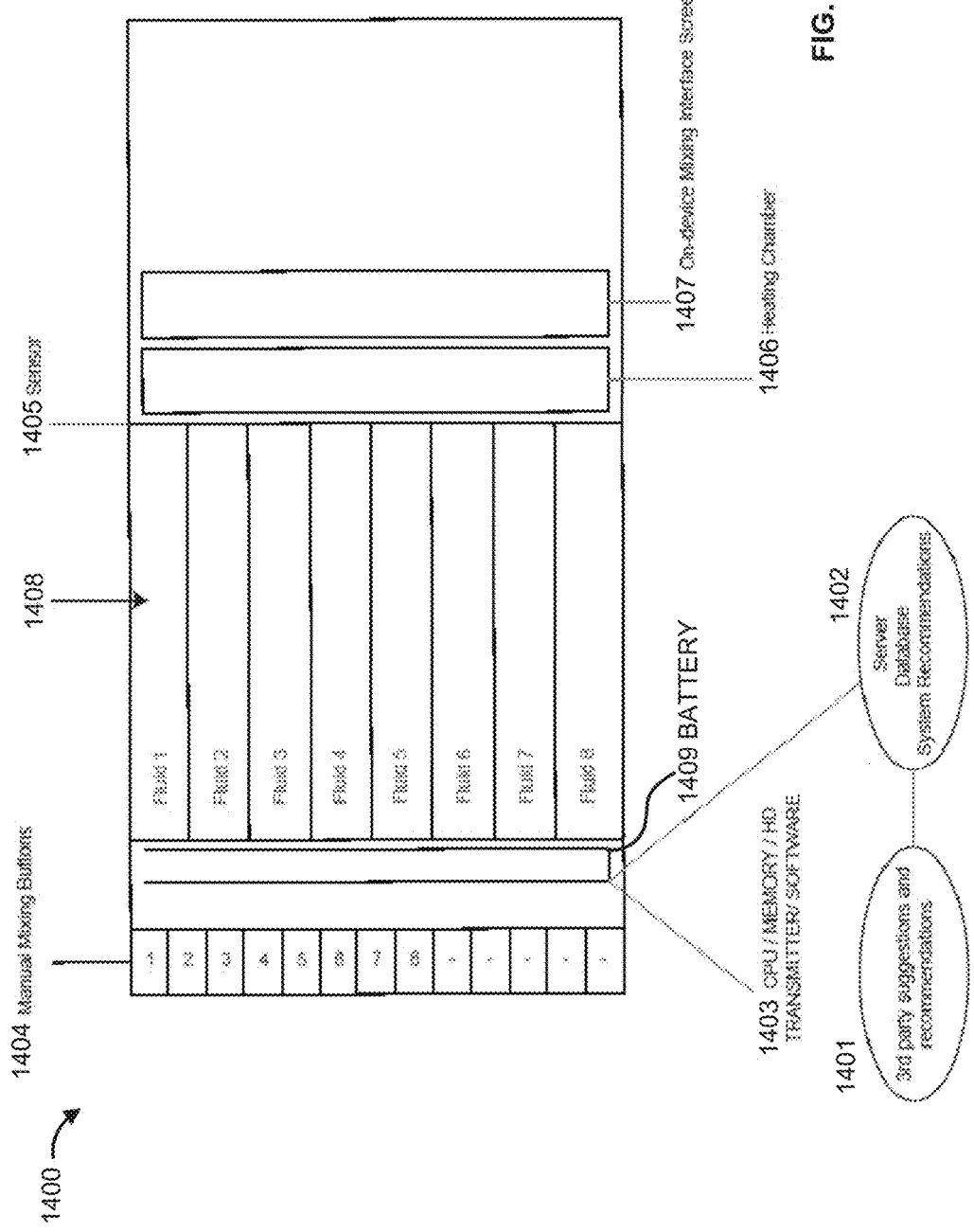
FIG. 14 illustrates an example vaporizer apparatus.

Referring to FIG. 14, different and variable vapor mixtures are provided from a personal vaporizer 1400, for example an electronic cigarette (e-cigarette) or the like may be provided by a system 1400. Different vaporizing fluids (e.g., fluids 1-8) are contained in multiple discrete chambers or containers 1408 of the vaporizing device and mixed together in defined ratios in order to create a desired formula, which is then heated to be utilized as vapor by the end user(s). The mix or fluids may be stored in contiguous chambers with individual dispensers leading to an independent mixing point, so as to avoid unwanted residual mixing. The chambers may be made of metal, polycarbonate, polymer, or other structural and impervious material and may be refillable and cleanable.

The personal vaporizer 1400 may include a processor 1403 controlling a vaporizing component 1406 of the personal vaporizer according to data received from an external source, e.g., a central server 1402. The rate at which the vaporizer 1400 vaporizes a particular material may be controlled to one or more proscribed levels or times set by the user, a caregiver, a recommendation system, a social network or other third party, via processor control of a heating elements and mixing chamber component 1406, sometimes referred to herein as a vaporizer or vaporizing component. The rate may be to an absolute rate, such as a defined power level for the component, or may be defined relative to a vaporization rate of another material (such as for example a ratio, e.g. "10% material 'A'/90% material 'B') or to a baseline rate (such as for example 50% of full power). The personal vaporizer 1400 may include, in association with the processor 1403, ancillary components such as a memory, battery 1409 or other power source, and input and output ports to the processor (not shown).

An array of liquid ports corresponding to the containers 1408 may be used to admit different mixtures of multiple liquids to the vaporizing component 1406, under control of the processor 1403. Use of a particular mixture of vaporizing fluids may be manually controlled via one or more manual mixing buttons 1404, which may be configured as software, hardware, firmware, or some combination of the foregoing, and which may be implemented in a graphical user interface of an ancillary device or integrated display 1407. In the alternative, or in addition, the mixing buttons may comprise mechanical actuators, for example, any one or more of a switch, dial, knob, slider, or push button. The actuators may be mechanically or electrically linked to a vaporization control element, for example a power control for a heater vaporizer coupled for vaporizing a particular material, or a flow control element for releasing or providing a fluid material to a vaporizing component.

Activation of vaporization may be controlled by application of suction at an inhalation port (not shown). A drop in pressure at the vaporizing component 1406 may be electronically or mechanically sensed by the processor 1403 and/or component 1406, causing vaporization of a mix of fluid components determined by the processor 1403 and/or settings of the mix buttons 1404, with control of fluid dispensing by independently operated components of the vaporizer 1406 or components intervening between the vaporizer 1406 and containers 1408, for example an array of micro-valves controlled by the processor. In other words, suction may activate power to the vaporizing component 1406, with the mix of vaporizable fluids controlled by the processor 1403. To the end user, the device 1400 provides the satisfaction of various specifiable mixtures of vapor production in response to suction applied, while the composition of the vapor is controlled, and may vary with time. Thus, for example, the user may conveniently switch between different mixtures of vaporizing fluids without changing vaporizers.

The central server 1402 may be used to hold a user ID and to correlate that ID to a user's prescribed or desired conditions for utilizing the personal vaporizer 1400. The server may receive and process third party suggestions and recommendations 1401 for sharing favorite or recommended vapor recipes with friends or celebrities, for example. Control data, including but not limited to socially recommended recipes may be provided to the personal vaporizer via a port or receiver in the personal vaporizer or in an auxiliary device such as a docking station or package (not shown). A processor 1403 of the personal vaporizer 1400 receives the data and may dispense or mix one or more available fluids in corresponding chambers of the personal vaporizer 1400 to defined specifications as determined by the control data. The personal vaporizer 1400 may collect usage data during use and transmits the data to a designated network address, for example an address for a data management server.

A control scheme based on monitoring data may trigger a communication to the user via the personal vaporizer 1400 or other user interface. Such communication may include inquiring whether a user is interested in replenishing one or more vaporizable materials, once a supply or prescribed amount of material has been consumed. A communication session directed at resupplying material or reauthorizing a prescribed use of material may include a remote transaction option enabling the user to complete a commercial or other transaction enabling supply of and/or vaporization of additional material, and/or to further use of the personal vaporizer itself. This may include, for example, providing information via the vaporizer or other user interface to a nearby kiosk or the like to enable resupply of additional vaporizable material to the personal vaporizer.

Various electronic personal vaporizing devices are known in the art, and are frequently being improved on. For example, details of a recent "Vapor Delivery Device" are disclosed by the inventor hereof in U.S. Patent Publication No. 2015/0047661, incorporated herein by reference. While the referenced publication provides a pertinent example of a personal vaporizer, it should be appreciated that various different designs for personal vaporizing devices are known in the art and may be adapted for use with the technology disclosed herein by one of ordinary skill. In addition, similar portable and personal devices for nebulizing liquids to create a mist for inhalation should be considered as generally encompassed within the meaning of "personal vaporizer" as used herein.

Figure 15:
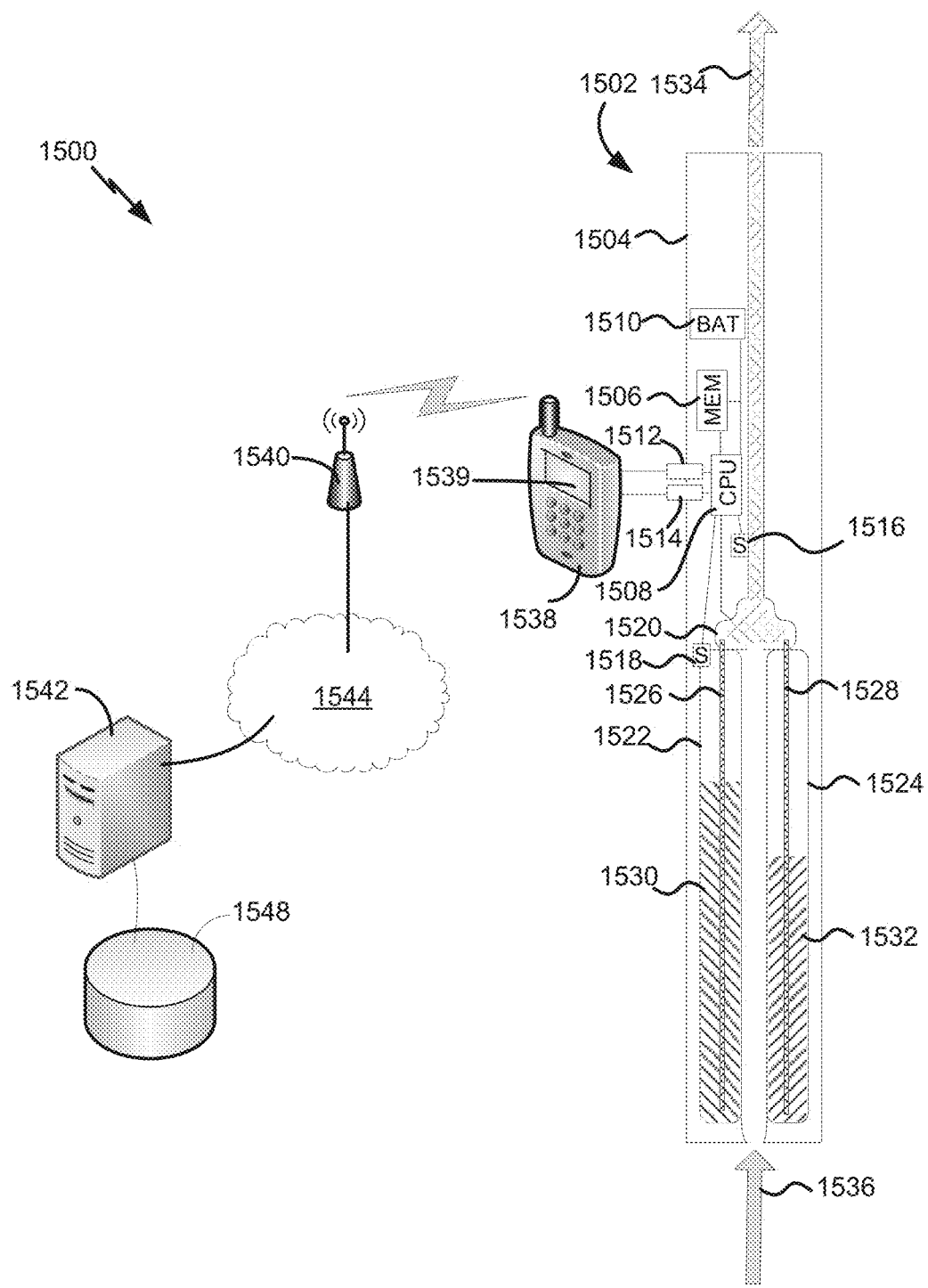
FIG. 15 illustrates an example vaporizer apparatus and operating environment.

Referring to FIG. 15, alternative aspects of a system 1500 including a multi-chambered personal vapor device with blend control are illustrated. The system 1500 may include an assembly 1502 for vaporizing a vaporizing fluid at a controlled rate, and for combining vaporization of two or more different fluids in a controlled manner. The assembly 1502 includes at least one container 1522 holding a vaporizable material 1530, sometimes referred to herein as a "first" container 1522 and "first" vaporizable material. In an aspect, the different vaporizable materials may be a fluid, such as a compressed gas, compressed liquid (e.g., a liquefied gas), or uncompressed liquid. Various suitable fluids are known in the art, for example, solutions of nicotine in glycerin, with or without flavor-enhancing agents, are known. In the alternative, or in addition, the first vaporizable material may be, or may include, a solid material. For embodiments using uncompressed liquids, the container 1522 may include a wick 1526 of absorbent material (e.g., cotton fiber) that carries the liquid to the vaporizing component 1520. Although the wick 1526 is shown only in the center of the container 1522 for illustrative clarity, it should be appreciated that the wick may substantially fill the container 1522. The container 1522 may be made of any suitable structural material, for example, an organic polymer, metal, ceramic, composite or glass material. Structural plastics may be preferred for disposable embodiments. The apparatus 1502 may include one or more additional or "second" containers 1524 (one of potentially many shown), each configured similarly with a wick 1528 if suitable for the particular second vaporizable material 1532 being contained.

A vaporizer 1520 may be coupled to the first container 1522 and to any additional containers, e.g., second container 1524. For example, coupling may be via wicks 1526, 1524, via a valve, or by some other structure. The coupling mechanism may operate independently of gravity, such as by capillary action or pressure drop through a valve. The vaporizer 1520 is configured to vaporize the different vaporizable materials from the first container 1522 and any additional containers 1524 at controlled rates; in operation, the vaporizer vaporizes or nebulizes the material, producing an inhalable mist. In embodiments, the vaporizer may include a heater coupled to a wick, or a heated wick. A heating circuit may include a nickel-chromium wire or the like, with a temperature sensor (not shown) such as a thermistor or thermocouple. Within definable limits, by controlling suction-activated power to the heating element, a rate of vaporization may be controlled. At minimum, control may be provided between no power (off state) and one or more powered states. Other control mechanisms may also be suitable.

A processor 1508 is coupled to the vaporizer via an electrical circuit, configured to control a rate at which the vaporizer 1520 vaporizes the different vaporizable materials. In operation, the processor supplies a control signal to the vaporizer 1520 that controls each vaporization rate of vaporization for each substance 1530, 1532 (two of many shown). A receiver port 1512 is coupled to the processor, and the processor receives data determining each vaporization rate and mix of different materials (e.g., a vapor recipe) from the receiver port. Thus, the vaporization rate and mix are remotely controllable, by providing the data.

The processor 1508 may be, or may include, any suitable microprocessor or microcontroller, for example, a low-power application-specific controller (ASIC) designed for the task of controlling a vaporizer as described herein, or (less preferably) a general-purpose central processing unit, for example, one based on 80×86 architecture as designed by Intel™ or AMD™, or a system-on-a-chip as designed by ARM™. The processor 1508 may be communicatively coupled to auxiliary devices or modules of the vaporizing apparatus 1502, using a bus or other coupling. Optionally, the processor 1508 and some or all of its coupled auxiliary devices or modules may be housed within or coupled to a housing 1504, substantially enclosing the containers 1524, 1524, the vaporizer 1520, the processor 1508, the receiver port 1512, and other illustrated components. The assembly 1502 and housing 1504 may be configured together in a form factor of an electronic cigarette, an electronic cigar, an electronic hookah, a hand-held personal vaporizer, or other desired form.

In related aspects, the assembly 1502 includes a memory device 1506 coupled to the processor 1508. The memory device 1506 may include a random access memory (RAM) holding program instructions and data for rapid execution or processing by the processor during control of the vaporizer 1502. When the vaporizer 1502 is powered off or in an inactive state, program instructions and data may be stored in a long-term memory, for example, a non-volatile magnetic, optical, or electronic memory storage device, which is not separately shown. Either or both of the RAM or the storage device may comprise a non-transitory computer-readable medium holding program instructions, that when executed by the processor 1508, cause the apparatus 1502 to perform a method or operations as described herein. Program instructions may be written in any suitable high-level language, for example, C, C++, C#, or Java™, and compiled to produce machine-language code for execution by the processor. Program instructions may be grouped into functional modules, to facilitate coding efficiency and comprehensibility. It should be appreciated that such modules, even if discernable as divisions or grouping in source code, are not necessarily distinguishable as separate code blocks in machine-level coding. Code bundles directed toward a specific type of function may be considered to comprise a module, regardless of whether or not machine code on the bundle can be executed independently of other machine code. In other words, the modules may be high-level modules only.

In a related aspect, the processor 1508 receives a user identifier and stores the user identifier in the memory device 1506. A user identifier may include or be associated with user biometric data, that may be collected by a biometric sensor or camera included in the assembly 1502 or in a connected or communicatively coupled ancillary device 1538, such as, for example, a smart phone executing a vaporizer interface application. The processor 1508 may generate data indicating a quantity of the different vaporizable materials 1530, 1532 consumed by the vaporizer 1520 in a defined period of time, and save the data in the memory device 1506. The processor 1508 and other electronic components may be powered by a suitable battery 1510, as known in the art, or other power source.

The assembly 1502 may include a sensor 1516, or multiple sensors 1516, 1518, to provide measurement feedback to the processor. For example, a sensor 1516 may be positioned downstream of the vaporizer, and the processor may derive the data used for controlling vaporization rate at least in part by interpreting a signal from the sensor correlated to a quantity of vapor emitted by the vaporizer. For further example, a sensor 1518 positioned upstream of the vaporizer, and the processor may derive the data at least in part by interpreting a signal from the sensor correlated to an amount of the different vaporizable materials remaining in the container, or to an amount of the different vaporizable materials passed from the containers to the vaporizer, or both. "Downstream" and "upstream" relate to the direction of air flow or air/vapor mixture flow through the apparatus 1502, as illustrated by discharge arrow 1534 and inlet 1536. Suction applied at a tip draws inlet air 1536 through the vaporizer 1520, discharging a vapor/air mixture 1535 at the tip. Sensors 1516, 1518 may include, for example, optical sensors, temperature sensors, motion sensors, flow speed sensors, microphones or other sensing devices.

In related aspects, the assembly may include a transmitter port 1514 coupled to the processor. The memory 1506 may hold a designated network address, and the processor 1508 may provide data indicating the quantity of the different vaporizable materials consumed by the vaporizer to the designated network address in association with the user identifier, via the transmitter port 1514.

An ancillary device, such as a smartphone 1538, tablet computer, or similar device, may be coupled to the transmitter port 1514 via a wired or wireless coupling. For example, the apparatus 1502 may include a serial port, for example a USB port, coupled to receiver and transmitter inputs to the processor 1508. In the alternative, or in addition, a wireless port (not shown) using Wifi (IEEE 802.11), Bluetooth, infrared, or other wireless standard may be coupled to the processor 1508. The ancillary device 1538 may be coupled to the processor 1508 for providing user control input to vaporizer control process executing on the processor 1508. User control input may include, for example, selections from a graphical user interface or other input (e.g., textual or directional commands) generated via a touch screen, keyboard, pointing device, microphone, motion sensor, camera, or some combination of these or other input devices, which may be incorporated in the ancillary device 1538. A display 1539 of the ancillary device 1538 may be coupled to the processor 1508, for example via a graphics processing unit (not shown) integrated in the ancillary device 1538. The display 1539 may include, for example, a flat screen color liquid crystal (LCD) display illuminated by light-emitting diodes (LEDs) or other lamps, a projector driven by an LED display or by a digital light processing (DLP) unit, or other digital display device. User interface output driven by the processor 1508 may be provided to the display device 1539 and output as a graphical display to the user. Similarly, an amplifier/speaker or other audio output transducer of the ancillary device 1538 may be coupled to the processor 1508 via an audio processing system. Audio output correlated to the graphical output and generated by the processor 1508 in conjunction with the ancillary device 1538 may be provided to the audio transducer and output as audible sound to the user.

The ancillary device 1538 may be communicatively coupled via an access point 1540 of a wireless telephone network, local area network (LAN) or other coupling to a wide area network (WAN) 1544, for example, the Internet. A server 1542 may be coupled to the WAN 1544 and to a database 1548 or other data store, and communicate with the apparatus 1502 via the WAN and couple device 1539. In alternative embodiments, functions of the ancillary device 1539 may be built directly into the apparatus 1502, if desired.

The described technology may enable users to receive and control various different vapor blend recipes before or during vaporization, and implement the blend recipes on a suitably equipped vaporizer manually or automatically. The user, the user's doctor or authorized advisor, or other third party may remotely access and authorize activation of a vaporization device, for example, an electronic cigarette or the like, in one or more transactions. The transactions may be based at least in part on measurements of vaporizable material consumed at a vaporization device identified with a specific user. The transactions may enable a user to replenish supply of a vaporizable material or unlock permission to vaporize the material at a vaporizing device. This may be useful for ordinary commercial transaction, enforcing medically-based dose regimens, or other applications.

Figure 16:
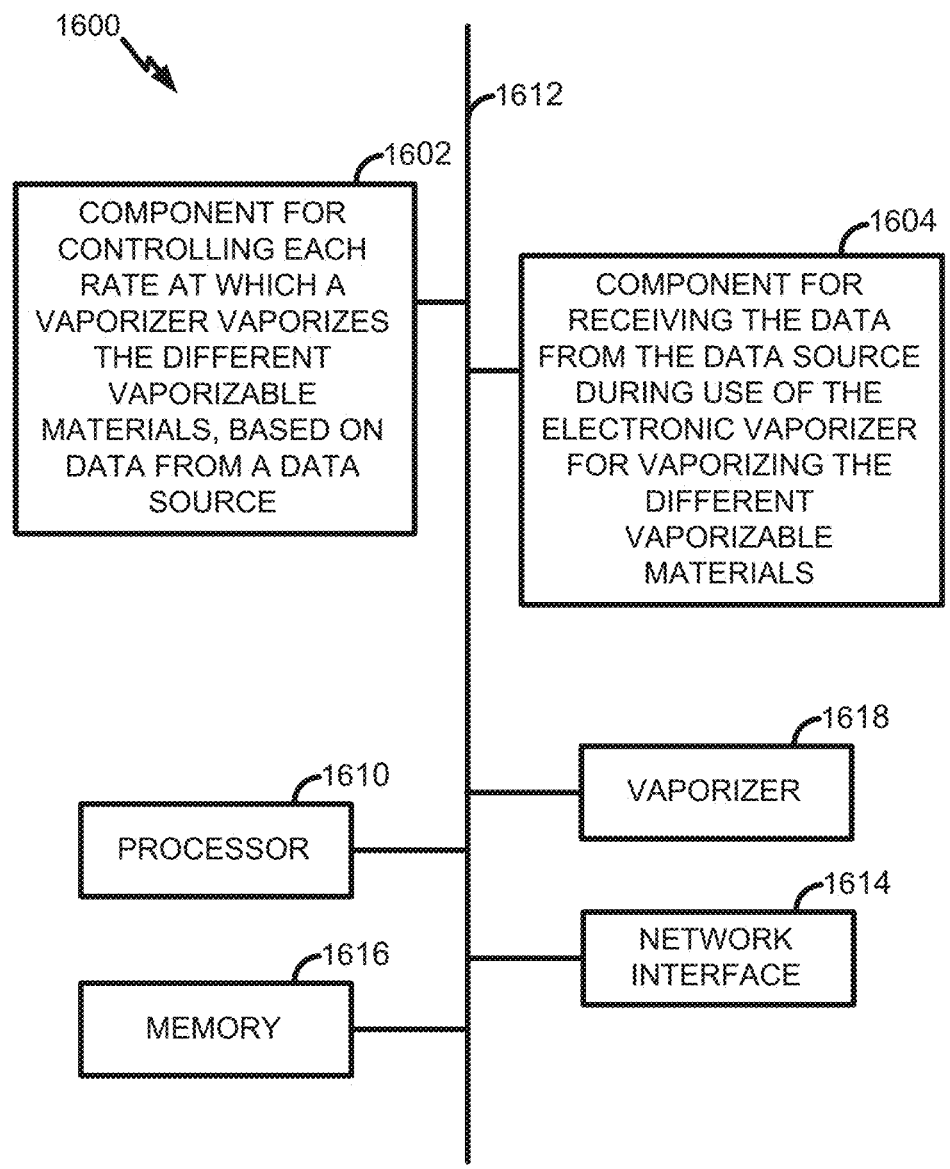
FIG. 16 illustrates example vaporizer apparatus.

FIG. 16 is a block diagram illustrating components of an apparatus or system 1600 for controlling a vaporizer based on parameter data that provides a customized vaporization blend, in accord with the foregoing examples. The apparatus or system 1600 may include additional or more detailed components as described herein. For example, the processor 1610 and memory 1616 may contain an instantiation of a controller for a vaporizer or nebulizer as described herein and other ancillary components. As depicted, the apparatus or system 1600 may include functional blocks that can represent functions implemented by a processor, software, or combination thereof (e.g., firmware).

As illustrated in FIG. 16, the apparatus or system 1600 may comprise an electrical component 1602 for controlling each vaporization rate at which a vaporizer vaporizes different vaporizable materials, based on data from a data source. The component 1602 may be, or may include, a means for controlling each vaporization rate at which a vaporizer vaporizes different vaporizable materials, based the data. Said means may include the processor 1610 coupled to the memory 1616, and to the network interface 1614 and a vaporizer 1618, the processor executing an algorithm based on program instructions stored in the memory. Such algorithm may include a sequence of more detailed operations, for example, as described in connection with methods disclosed herein.

The apparatus or system 1600 may further comprise an electrical component 1604 for receiving or obtaining the data specifying each vaporization rate during use of the electronic vaporizer for vaporizing the different vaporizable materials. The component 1604 may be, or may include, a means for receiving or obtaining the data specifying each vaporization rate during use of the electronic vaporizer for vaporizing the different vaporizable materials. Said means may include the processor 1610 coupled to the memory 1616, and to the network interface 1614, the processor executing an algorithm based on program instructions stored in the memory. Such algorithm may include a sequence of more detailed operations, for example, retrieving a network or memory address from the memory 1616, sending a query requesting the data to a network address or to a memory component, and receiving a transmission including the requested data from a server at the network address or from a memory component. In the alternative, or in addition, such algorithm may include receiving a data broadcast or unicast message including the data from the server or from a coupled ancillary device, without the broadcast or unicast message being preceded by a data request. For example, a server may transmit vaporization control parameters periodically or automatically as part of a device initiation process.

The apparatus 1600 may include a processor module 1610 having at least one processor, in the case of the apparatus 1600 configured as a controller configured to operate a dispenser/vaporizer 1618 and other components of the apparatus. The processor 1610, in such case, may be in operative communication with the memory 1616, interface 1614 or dispenser/vaporizer 1618 via a bus 1612 or similar communication coupling. The processor 1610 may effect initiation and scheduling of the processes or functions performed by electrical components 1602-1604.

In related aspects, the apparatus 1600 may include a network interface module operable for communicating with a server over a computer network. The apparatus may include a controllable dispenser for a vaporizable material, for example, a heat-driven or other vaporizer 1618 for which vaporization rate is correlated to power supplied, or a micro-valve for which vaporization is proportional to valve position. In further related aspects, the apparatus 1600 may optionally include a module for storing information, such as, for example, a memory device/module 1616. The computer readable medium or the memory module 1616 may be operatively coupled to the other components of the apparatus 1600 via the bus 1612 or the like. The memory module 1616 may be adapted to store computer readable instructions and data for enabling the processes and behavior of the modules 1602-1604, and subcomponents thereof, or of the methods disclosed herein. The memory module 1616 may retain instructions for executing functions associated with the modules 1602-1604. While shown as being external to the memory 1616, it is to be understood that the modules 1602-1604 can exist within the memory 1616.

Figure 17:
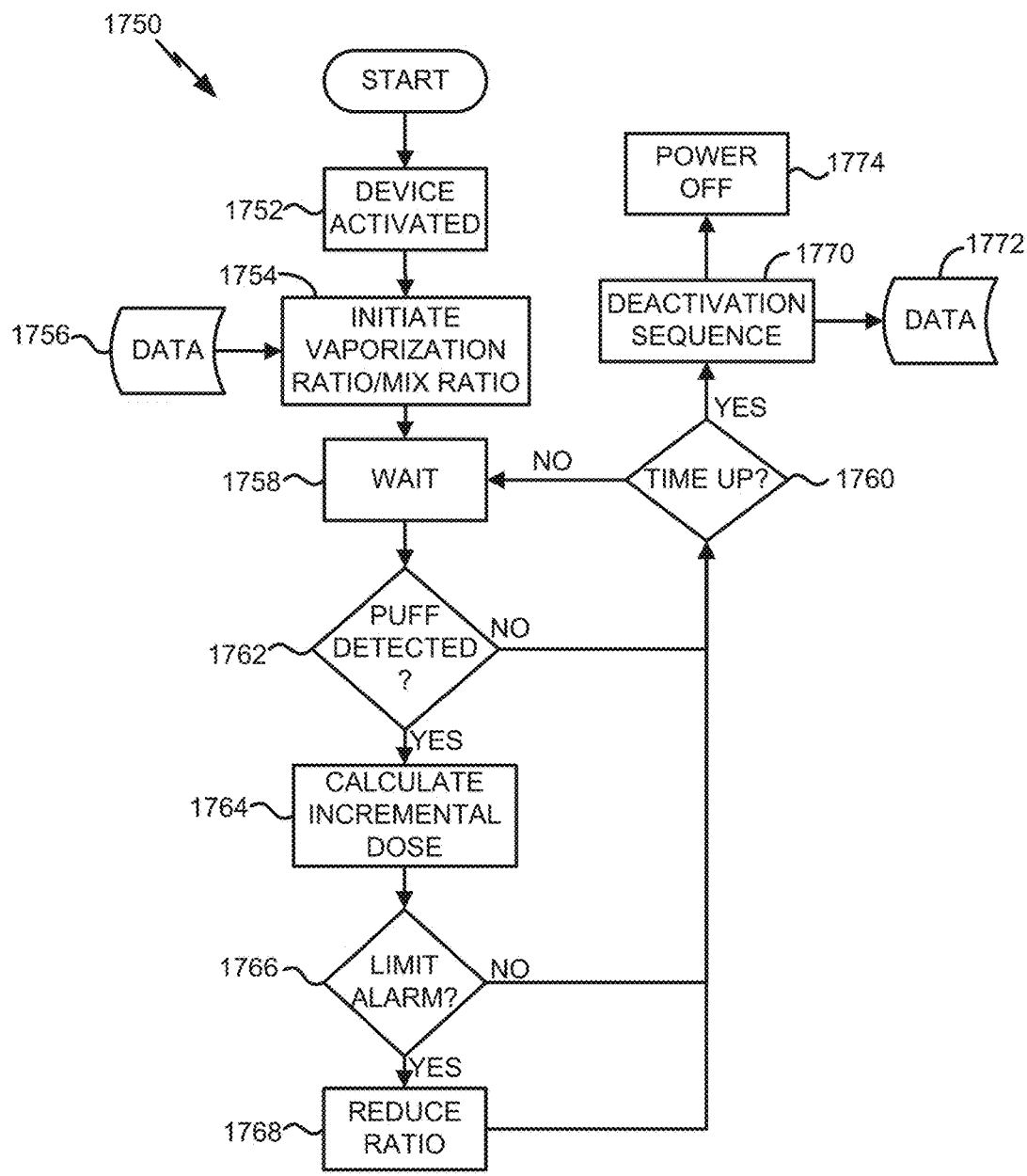
FIG. 17 illustrates an exemplary method.

An example of a control algorithm 1750 is illustrated by FIG. 17, for execution by a processor of a personal vaporizer as described herein, which includes independently controllable vaporization of at least two materials in a vapor blend. In the illustrated example, one of the materials may be active, and it is desired to control the dose based on time, user mass, or any other desired criteria. Remaining materials are inert, and any amount may be consumed. A ratio of 1 (one) indicates that 100% of the vapor produced is the active material. A ratio of 0 (zero) indicates that none of the vapor is active material, and hence 100% is the inert material. Intermediate ratios are possible, and may be desirable, to avoid abrupt changes in dose administration. The ratio may be controlled by allocating power to independent vaporization heaters allocated to the respective materials to be vaporized. In addition, any one or more active or inert vaporizable materials may be selected from a plural number of containers holding different materials. The selection of materials may make up a "mix" to be vaporized. A mix may include one or more active materials in which a dose rate is carefully controlled, or may not include any materials for which a dose is controlled. In the latter case, a mix may simply comprise a static vapor recipe that is unchanged until a new mix is called for in a predetermined plan or requested by a user.

The algorithm 1750 may be triggered by activation of the device at 1752, for example when a user takes an initial puff. Puffs taken before the control algorithm is operative may be controlled at a zero ratio, or 100% inert material. At 1754, the processor initiates a current vaporization ratio, based on locally stored and/or remotely obtained data 1756, including user identifier, past use records, the applicable control scheme, and any relevant criteria. For example, for a new user with no past use and a target dose well above that which can be achieved by a single puff, the processor may set the ratio equal to one. At 1758, the processor waits for the next puff, for example, by executing a wait loop.

Once a puff is detected at 1762, the processor estimates a puff volume and potency based on open loop data (e.g., the set ratio, known materials, and vaporization power), on feedback data (e.g., vapor opacity, flow rate, time), or some combination of open loop and feedback data, and from this calculates, at 1764, an incremental dose. At 1766, the processor determines whether a cumulative dose is approaching any limit that calls for reduction of the vaporization ratio to avoid an excess dose. This may be a simple "on" until exceeded, then "off" control scheme, or may be a form of more sophisticated control such as, for example, proportional control, proportional-integral (PI) control, or proportional-integral-derivative (PID) control. If real-time dose level from blood sensing or similar data is available, control may be benchmarked by a measured current dose. If actual dose measurements are not available, the dose may be estimated based on vaporization and puff data. If a reduction in dose is called for, the processor may reduce the control ratio by a calculated amount, at 1768. For example, in a proportional control scheme, the controller may reduce the ratio by an amount proportional to the estimated cumulative dose level relative to the targeted dose level. As the estimated cumulative dose approaches the target, therefore, the rate of reduction may increase.

If a request for a change in a mix ratio is detected at 1776, for example if the processor receives data specifying a change in the mix of materials to be vaporized, the processor may process an interruption sequence 1778 in which it creates a record of the interrupted dosing regimen or other plan at 1772, and reverts to an initiation process 1754 for initiating a new vaporization schedule. In an alternative, change in the vapor blend may be delayed so that a dosing schedule already in process is not interrupted, and the data for the change may be saved and used to initiate a new schedule at 1754 after the deactivation sequence 1770, instead of powering down. The processor may select one of these alternatives based on user input, or as part of a fixed design flow.

If no reduction is called for at 1766, or no puff is detected at 1762, and no request for change in a mix ratio is detected at 1776, the processor may determine, at 1760, whether the device has been inactive long enough trigger deactivation. If time is not elapsed, the processor may re-enter the wait loop 1758. If time is elapsed, the processor may initiate a deactivation sequence at 1770. The deactivation sequence 1770 may include, for example, storing a current time stamp and cumulative dose information in a data record 1772, which may be stored locally, and or remotely. Then, the processor may power off or enter a low-power "sleep" mode 1774.

Figure 18:
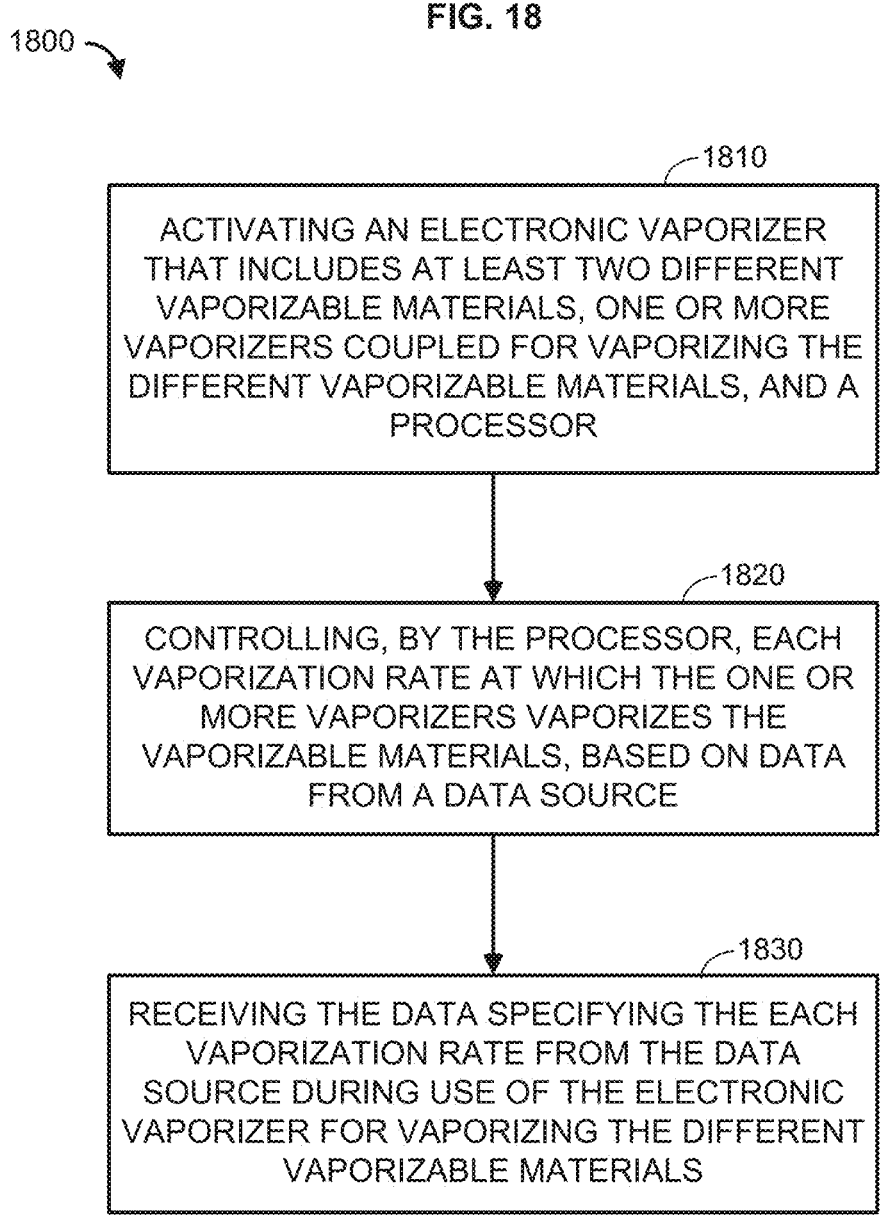
FIG. 18 illustrates an exemplary method.

In view the foregoing, and by way of additional example, FIG. 18, FIG. 19, FIG. 20, FIG. 21, and FIG. 22 show aspects of a method or methods for controlling a vaporizer, as may be performed by a personal vaporizing device as described herein, alone or in combination with other elements of the systems and apparatuses disclosed herein. Referring to FIG. 18, the method 1800 may include, at 1810, activating an electronic vaporizer that includes at least two containers for holding a different vaporizable material, one or more vaporizers coupled to the at least two container for vaporizing the different vaporizable materials, and a processor. For example, a puff sensor may detect a puff, and send an activation interrupt to a sleeping processor, which in response to the interrupt may power up the control circuitry of the vaporizer and begin an initialization sequence.

The method 1800 may further include, at 1820, controlling, by the processor, each vaporization rate at which the vaporizer vaporizes the vaporizable material, based on data from a data source. For example, the data may specify a user identifier, cumulative dose information with timestamp, and a metabolic decay profile for the user and applicable substance(s) to be vaporized. From this, the processor may calculate a ratio or other value that controls each vaporization rate or a relative rate at which one or more materials are vaporized in response to puff suction. "Relative rate" means a quantitative value or values defining the rate at which each component of a vapor blend is vaporized, relative to each other or to any other useful benchmark. For example, a value of F1 at 34% and F2 at 66% may indicate that a first fluid is vaporized at 33% of maximum rate and a second fluid at 66% of maximum rate; or it may indicate that the targeted vapor should be comprised of 34% F1 and 66% F2. Various different control values and schemes may be devised by one of ordinary skill, appropriate for the characteristics of the materials to be vaporized and the components to be used to perform the vaporization.

The method 1800 may further include, at 1830, receiving the data specifying each vaporization rate from a data source during use of the electronic vaporizer for vaporizing the different vaporizable materials. For example, the processor may at any time during operation of the vaporizer receive data from a connected smartphone or the like that specifies a vapor blend or recipe for one or more identified users. The specified blend may be static, or may vary over time according to a defined algorithm. "Specifying each vaporization rate" may include any one or more of defining a vaporization rate for each of the different vaporizable materials, defining control parameters known to achieve a specific vaporization rate for each of the different vaporizable materials, defining one or more parameters used to determine an output of a rate-control algorithm for each of the different algorithms, specifying a total rate for all materials to be vaporized and a proportionate share of the total assigned to each material, or any other data specifying a particular vapor blend.

In an alternative, a manually operated valve or pump may be used to control a rate at which a vaporization fluid is provided to vaporizer. The rate may be adjusted, for example, by turning a dial or moving a slider, or otherwise manipulating a mechanical actuator on an exterior of the assembly, which is linked to the pump or valve. In an alternative, user input may be provided through an electronic control panel (e.g., a touchscreen, keypad, or potentiometer). If an electronic control panel is used, data from the panel may be provided to the processor, which may control each valve or pump by generating and sending control signals via an electronic circuit, based on the panel input. The electronic control panel may be provided by a connected smartphone or the like that specifies a vapor blend or recipe for one or more identified users.

The method 1800 may include any one or more of additional operations in any operable order. Each of these additional operations is not necessarily performed in every embodiment of the method, and the presence of any one of the operations does not necessarily require that any other of these additional operations also be performed.

Figure 19:
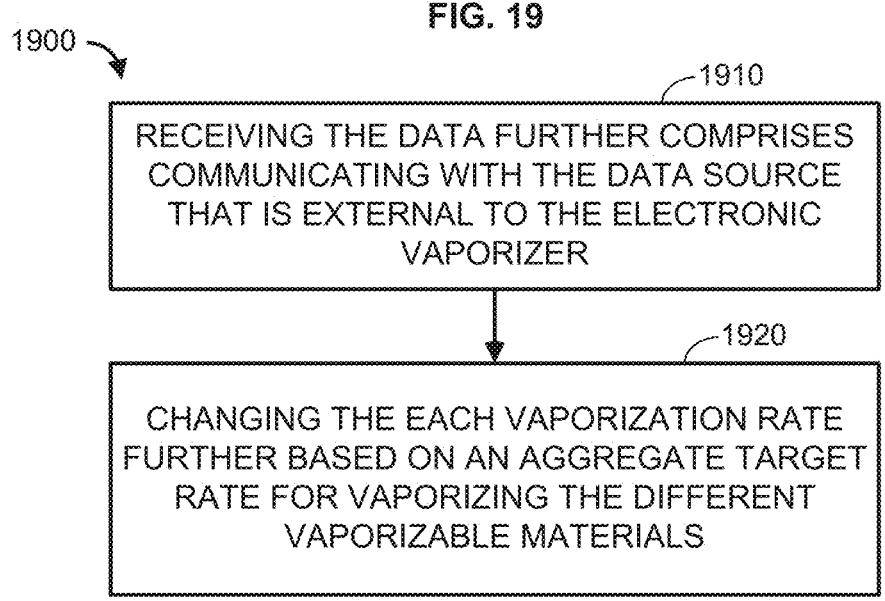
FIG. 19 illustrates an exemplary method.

Referring to FIG. 19 showing additional operations 1900, the method 1800 may further include, at 1910, communicating with the data source that is external to the electronic vaporize. The communicating may include, for example, pairing a personal vaporizer with an ancillary device, for example a smartphone, using a Bluetooth or other wireless link, or a serial (e.g., USB). Transmitted data may be encrypted and secured using any suitable method.

The method 1800 may include, at 1920, changing each vaporization rate further based on an aggregate target rate for vaporizing the different vaporizable materials. For example, an aggregate rate defined by a specified opacity or mass per unit volume may be specified. A vapor recipe may include both absolute and relative values. A blend may be unchanged while the density of the vapor is varied, if desired.

Referring to FIG. 20 showing additional operations 1000, the method 1800 may further include, at 2010, obtaining the data for a specific user from an authorized medical provider, wherein the data is based on a medically prescribed dose for the specific user. For example, a user may communicate a provider network address and patient identifier to the processor using a smartphone or the like. The processor of the personal vaporizer or ancillary device may transmit the patient identifier to a server at the medical provider address, and after negotiating an authentication process, receive data defining a prescription for a particular vapor blend. This prescription data may be stored in a memory of the vaporizer and used at a desired time to administer a medication to the specified patient.

Similarly, the method 1800 may further include, at 2020, obtaining an identifier for a defined flavor, wherein the data includes a formula for producing a vapor having the defined flavor. For example, the formulae may be requested from a vendor or distributor website, in exchange for a small fee or for free. Likewise, the method 1800 may include, at 2030, obtaining the data based on an identifier for a human health objective, wherein the data includes a formula for producing a vapor having a composition designed for achieving the human health objective. For example, a user may desire to reduce cancer risk, strengthen an immune response, go to sleep, reduce stress, increase alertness, or receive essential vitamins. The user may, through the vaporizer or coupled ancillary device, send the objective to a nutraceutical or herbal remedy supplier, and receive data defining a formula for achieving the desired objective. The formula may be saved in a memory of the device or an ancillary device for obtaining a supply of the necessary vaporizable components and controlling the vapor blend during use. Dose may be controlled as described previously herein.

The method 1800 may further include, at 2040, obtaining the data based on an identifier for a recreational objective, wherein the data includes a formula for producing a vapor having a composition designed for achieving the recreational objective. For example, the user may select one or more flavors it is desired to experience for recreational reasons. A formula may be obtained and used as for other purposes. Likewise, the method may include, at 2050, receiving user preference information and determining the data based at least in part on the user preference information. For example, the user preference information may include ranked lists of preferred flavoring agents for different times of day, and the processor may select the highest ranked choice contained in the vaporizer based on the time of day. Many other uses of preference data are possible.

Referring to FIG. 21 showing additional operations 2100, the method 1800 may further include, at 2110 receiving the data formatted according to a computer network protocol via a receiver port coupled to the processor. The method may further include, at 2120, communicating with an external server via a computer network to obtain the data. The method may further include, at 2130, confirming that the data is authorized for controlling each vaporization rate, based on an access license granted by a user of the apparatus to an identified person. For example, a user may grant to a trusted friend or advisor an ability to specify a blend ratio for vapor to be produced by the user's vaporizer. Such grants may be made in any suitable manner, but convenient approaches may include interfacing with a social networking system through an API or the like. Thus, a user may identify trusted "vaping" friends or advisors in the social network, and supply the personal vaporizing system with his user identifier and access authorization for receiving the blend formulas from the designated friends. Accordingly, at 2140, the method 1800 may include determining the access license, based on a relationship status of the identified person in social network data for the user obtained from a social networking server.

Disclosed is an electronic vapor device comprising a vapor outlet, a first container for storing a first vaporizable material, a second container for storing a second vaporizable material, a first vaporizer component coupled to the first container configured for vaporizing the first vaporizable material at a first vaporization rate to generate a first vapor and for providing the first vapor to the vapor outlet, and a second vaporizer component coupled to the processor the second container configured for vaporizing the second vaporizable material at a second vaporization rate to generate a second vapor and for providing the second vapor to the vapor outlet. The vaporizer component and the second vaporizer component can vaporize the first vaporizable material and the second vaporizable material, respectively, in serial or simultaneously.

The electronic vapor device can further comprise a mixing chamber coupled to the first vaporizer component and the second vaporizer component to receive the first vapor and the second vapor, to mix the first vapor and the second vapor and, to provide the mixed vapor to the vapor outlet. A composition of the mixed vapor varies based on at least one of the first vaporization rate and the second vaporization rate.

The electronic vapor device can further comprise a processor, configured for determining the first vaporization rate and the second vaporization rate and for providing the first vaporization rate to the first vaporizer component and the second vaporization rate to the second vaporizer component. The processor can be further configured to independently control the first vaporization rate and the second vaporization rate. The electronic vapor device can further comprise a network access device, and wherein the processor can be further configured to receive the first vaporization rate and the second vaporization rate from a remote server via the network access device. The processor can be configured to receive data from the remote server indicating a medically prescribed dose of at least one of the first vaporizable material and the second vaporizable material and for determining the first vaporization rate and the second vaporization rate based on the data. The processor can be configured to receive data from the remote server indicating a formula for producing a specific flavor of vapor and for determining the first vaporization rate and the second vaporization rate based on the data. The processor can be configured to determine that a user of the electronic vapor device has access rights to the formula. The processor can be further configured to adjust at least one of the first vaporization rate and the second vaporization rate during use of the electronic vapor device.

The electronic vapor device can further comprise an input device configured for receiving the first vaporization rate and the second vaporization rate. The input device can comprise one or more of, a touchscreen, a switch, a dial, a knob, a slider, or a button.

Referring to FIG. 22, a method 2200 is disclosed comprising determining a first vaporization rate and a second vaporization rate at 2210. Determining the first vaporization rate and the second vaporization rate can comprise determining a formula for a mixed vapor and determining the first vaporization rate and the second vaporization rate based on the formula. The method 2200 can further comprise determining that a user has access rights to the formula. The method 2200 can further comprise determining an amount of the first vaporizable material based on the first vaporization rate, determining an amount of the second vaporizable material based on the second vaporization rate, withdrawing the amount of the first vaporizable material into a first vaporizer component for vaporization, and withdrawing the amount of the second vaporizable material into a second vaporizer component for vaporization. Determining the first vaporization rate and the second vaporization rate can comprise receiving data indicative of the first vaporization rate and the second vaporization rate from a remote server via a network access device. The data can indicate a medically prescribed dose of at least one of the first vaporizable material and the second vaporizable material and wherein the first vaporization rate and the second vaporization rate are determined based on the data.

The method 2200 can comprise vaporizing a first vaporizable material based on the first vaporization rate to create a first vapor at 2220. The method 2200 can comprise vaporizing a second vaporizable material based on the second vaporization rate to create a second vapor at 2230. Vaporizing the first vaporizable material based on the first vaporization rate to create the first vapor and vaporizing the second vaporizable material based on the second vaporization rate to create the second vapor are performed in serial or simultaneously.

The method 2200 can comprise expelling the first vapor and the second vapor through an exhaust port for inhalation by a user at 2240. The method 2200 can further comprise receiving the first vapor and the second vapor into a mixing chamber to mix the first vapor and the second vapor and expelling the mixed vapor through the exhaust port for inhalation by a user.

The methods disclosed may include any one or more of additional operations of any other method in any operable order. Each of these additional operations is not necessarily performed in every embodiment of the method, and the presence of any one operation does not necessarily require that any other additional operations also be performed.

In view of the exemplary systems described supra, methodologies that can be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks can be required to implement the methodologies described herein. Additionally, it should be further appreciated that the methodologies disclosed herein are capable of being stored on an article of manufacture to facilitate transporting and transferring such methodologies to computers.

Those of skill would further appreciate that the various illustrative logical blocks, modules, circuits, and algorithm steps described in connection with the aspects disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

As used in this application, the terms "component," "module," "system," and the like are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components may reside within a process and/or thread of execution and a component can be localized on one computer and/or distributed between two or more computers.

As used herein, a "vapor" includes mixtures of a carrier gas or gaseous mixture (for example, air) with any one or more of a dissolved gas, suspended solid particles, or suspended liquid droplets, wherein a substantial fraction of the particles or droplets if present are characterized by an average diameter of not greater than three microns. As used herein, an "aerosol" has the same meaning as "vapor," except for requiring the presence of at least one of particles or droplets. A substantial fraction means 10% or greater; however, it should be appreciated that higher fractions of small (<3 micron) particles or droplets can be desirable, up to and including 100%. It should further be appreciated that, to simulate smoke, average particle or droplet size can be less than three microns, for example, can be less than one micron with particles or droplets distributed in the range of 0.01 to 1 micron. A vaporizer may include any device or assembly that produces a vapor or aerosol from a carrier gas or gaseous mixture and at least one vaporizable material. An aerosolizer is a species of vaporizer, and as such is included in the meaning of vaporizer as used herein, except where specifically disclaimed.

Various aspects presented in terms of systems can comprise a number of components, modules, and the like. It is to be understood and appreciated that the various systems may include additional components, modules, etc. and/or may not include all of the components, modules, etc. discussed in connection with the figures. A combination of these approaches can also be used.

In addition, the various illustrative logical blocks, modules, and circuits described in connection with certain aspects disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, system-on-a-chip, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein can be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, a DVD disk, or any other form of storage medium known in the art. An exemplary storage medium is coupled to the processor such the processor can read information from, and write information to, the storage medium. In the alternative, the storage medium can be integral to the processor. The processor and the storage medium may reside in an ASIC or may reside as discrete components in another device.

Furthermore, the one or more versions can be implemented as a method, apparatus, or article of manufacture using standard programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Those skilled in the art will recognize many modifications can be made to this configuration without departing from the scope of the disclosed aspects.

The previous description of the disclosed aspects is provided to enable any person skilled in the art to make or use the present disclosure. Various modifications to these aspects will be readily apparent to those skilled in the art, and the generic principles defined herein can be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

The invention claimed is:

1. An electronic vapor device comprising:
a device processor operable for controlling the electronic vapor device;

a plurality of containers, wherein the plurality of containers includes at least a first container type and a second container type, wherein each first container type is configured to store a first vaporizable material, wherein each second container type is configured to store a second vaporizable material:

a first vaporizing component operatively coupled to the device processor and controlled in part by the device processor, wherein the first vaporizing component is in fluid communication with at least one first container type for receiving a first vaporizable material therefrom, wherein the first vaporizing component is operable to vaporize the vaporizable material received therein to generate a first vapor therefrom;

a second vaporizing component operatively coupled to the device processor and controlled in part by the device processor, wherein the second vaporizing component is in fluid communication with at least one second container type for receiving a second vaporizable material therefrom, wherein the second vaporizing component is operable to vaporize the vaporizable material received therein to generate a second vapor therefrom;

at least one vapor outlet coupled to at least one of the first vaporizing component and the second vaporizing component, wherein the at least one vapor outlet is configured to receive at least one of a first vapor generated by the first vaporizing component, a second vapor generated by the second vaporizing component, and combinations thereof, the at least one vapor outlet operable to expel at least one of the first vapor, the second vapor, and combinations thereof from the electronic vapor device; and at least one power source operatively coupled to the first vaporizing component and the second vaporizing component, wherein the at least one power source is operable to generate a supply of power for operation of at least the first vaporizing component, the second vaporizing component, and combinations thereof.

2. The electronic vapor device of claim 1, wherein the first vaporizing component is configured to operate at least one of independently of the second vaporizing component and simultaneously with the second vaporizing component; and wherein the second vaporizing component is configured to operate at least one of independently of the first vaporizing component and simultaneously with the first vaporizing component.

3. The electronic vapor device of claim 1, further comprising a blending component operatively coupled to the device processor and controlled in part by the device processor, wherein the blending component is in fluid communication with the first vaporizing component for receiving at least one of at least a portion of a first vapor generated by the first vaporizing component, at least a portion of a second vapor generated by the second vaporizing component, and combinations thereof, wherein the blending component is operable to blend at least a portion of the first vapor and the second vapor received therein to create a mixed vapor, wherein the blending component is coupled to the at least one vapor outlet for expelling at least a portion of the mixed vapor therefrom.

4. The electronic vapor device of claim 1, further comprising:

a mixing component operatively coupled to the device processor and controlled in part by the device processor, wherein the mixing component is in fluid communication with the plurality of containers for receiving at least a portion of material therefrom, wherein the mixing component is operable to withdraw a selected amount of first vaporizable material from the at least one first container type and deliver at least a portion of the selected amount of vaporizable material withdrawn therefrom to the first vaporizing component, wherein the mixing component is operable to withdraw a selected amount of second vaporizable material from the at least one second container type and deliver at least a portion of the selected amount of vaporizable material withdrawn therefrom to the second vaporizing component.

5. The electronic vapor device of claim 4, wherein the device processor is operable to:

obtain data associated with at least one of at least one operational parameter of the mixing component, at least one operational parameter of the first vaporizing component, at least one operational parameter of the second vaporizing component, at least one characteristic of a first vaporizable material contained in at least one first container type, at least one characteristic of a second vaporizable material contained in at least one second container type, user data associated with at least one user of the electronic vapor device, and combinations thereof;

determine, in response to at least a portion of the obtained data, at least one device configuration for at least one of vaporizing a first vaporizable material contained in at least one first container type, vaporizing a second vaporizable material contained in at least one second container type, and combinations thereof; and generate at least one control signal for controlling at least one operational parameter of the electronic vapor device in accordance with the at least one device configuration.

6. The electronic vapor device of claim 5, wherein the device processor is operable to generate at least one vaporizing control signal for controlling at least one operational parameter of the first vaporizing component for vaporizing a first vaporizable material withdrawn from at least one first container type.

7. The electronic vapor device of 5, wherein the device processor is operable to generate at least one vaporizing control signal for controlling at least one operational parameter of the second vaporizing component for vaporizing a second vaporizable material withdrawn from at least one second container type.

8. The electronic vapor device of claim 5, wherein the device processor is operable to generate at least one mixing control signal for controlling at least one operational parameter of the mixing component for withdrawing a selected amount of first vaporizable material from at least one first container type, withdrawing a selected amount of second vaporizable material from at least one second container type, and combinations thereof.

9. The electronic vapor device of claim 5, further comprising at least one input/output device operatively coupled to the device processor and controlled in part by the device processor, wherein the at least one input/output device is configured to receive a plurality of commands for controlling at least one operational parameter of the electronic vapor device for at least one of vaporizing a first vaporizable material withdrawn from at least one first container type by the first vaporizing component, vaporizing a second vaporizable material withdrawn from at least one second container type by the second vaporizing component, and combinations thereof, and to transmit the plurality of commands to the device processor;

wherein the device processor is operable to generate at least one control signal for controlling at least one operational parameter of the electronic vapor device in accordance with at least one command of the plurality of commands.

10. The electronic vapor device of claim 9, wherein the at least one input/output device comprises a user interface, wherein at least a portion of the plurality of commands are received from an associated user via the user interface.

11. The electronic vapor device of claim 9, wherein the at least one input/output device is further configured to operatively connect the device processor to a remote device, wherein at least a portion of the plurality of commands are received from the remote device via the at least one input/output device.

* * * * *